United States Patent
Kimura et al.

(10) Patent No.: US 10,202,376 B2
(45) Date of Patent: Feb. 12, 2019

(54) HETEROCYCLIC COMPOUND

(71) Applicant: Takeda Pharmaceutical Company Limited, Chuo-ku, Osaka-shi, Osaka (JP)

(72) Inventors: Eiji Kimura, Kanagawa (JP); Yuhei Miyanohana, Kanagawa (JP); Masaki Ogino, Kanagawa (JP); Yuta Tanaka, Kanagawa (JP); Makoto Fushimi, New York, NY (US); Tomohiro Okawa, Kanagawa (JP); Yuki Hanya, Tokyo (JP); Tatsuki Koike, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 15/538,297

(22) PCT Filed: Dec. 21, 2015

(86) PCT No.: PCT/JP2015/085689
§ 371 (c)(1),
(2) Date: Jun. 21, 2017

(87) PCT Pub. No.: WO2016/104434
PCT Pub. Date: Jun. 30, 2016

(65) Prior Publication Data
US 2017/0362223 A1    Dec. 21, 2017

(30) Foreign Application Priority Data

Dec. 24, 2014 (JP) .................. 2014-259662

(51) Int. Cl.
| | |
|---|---|
| C07D 471/04 | (2006.01) |
| A61K 31/437 | (2006.01) |
| C07D 487/04 | (2006.01) |
| A61P 25/00 | (2006.01) |
| A61P 29/00 | (2006.01) |

(52) U.S. Cl.
CPC ............ *C07D 471/04* (2013.01); *A61P 25/00* (2018.01); *A61P 29/00* (2018.01); *C07D 487/04* (2013.01)

(58) Field of Classification Search
CPC .................................. C07D 471/04
See application file for complete search history.

(56) References Cited

U.S. PATENT DOCUMENTS

| | | | |
|---|---|---|---|
| 4,382,938 A | 5/1983 | Kaplan et al. | |
| 5,252,563 A | 10/1993 | Cordi et al. | |
| 5,672,469 A | 9/1997 | Hioki et al. | |
| 5,840,732 A | 11/1998 | Takatani et al. | |
| 2003/0119811 A1 | 6/2003 | Liverton et al. | |
| 2004/0147568 A1 | 7/2004 | Yu et al. | |
| 2004/0204409 A1 | 10/2004 | Ando et al. | |
| 2010/0331335 A1 | 12/2010 | Sham et al. | |
| 2012/0258950 A1 | 10/2012 | Andrews et al. | |
| 2013/0072494 A1 | 3/2013 | Sham et al. | |

FOREIGN PATENT DOCUMENTS

| | | |
|---|---|---|
| JP | 2004-161716 A | 6/2004 |
| WO | WO 2012/174199 A1 | 12/2012 |

OTHER PUBLICATIONS

Iadarola et al. Ther Adv Chronic Dis 2015, vol. 6(3) 97-114.*
Wu et al. Neurotherapeutics, vol. 6, No. 4, 2009, p. 693-702.*
Jin et al., "Developmental Expression, Subcellular Localization, and Tyrosine Phosphorylation of NR2A and NR2B in the Rat Brain," Mol. Cells, 1997, 7(1):64-71.
Monyer et al., "Developmental and Regional Expression in the Rat Brain and Functional Properties of Four NMDA Receptors," Neuron, Mar. 1994, 12:529-540.
Shityakov et al,. "α-Cyclodextrin dimer complexes of dopamine and levodopa derivatives to assess drug delivery to the central nervous system: ADME and molecular docking studies," International Journal of Nanomedicine, 2012, 7:3211-3219.
Watanabe et al., "Distinct Distributions of Five N-Methyl-D-Aspartate Receptor Channel Subunit mRNAs in the Forebrain," The Journal of Comparative Neurology, 1993, 338:377-390.

* cited by examiner

*Primary Examiner* — Emily A Bernhardt
(74) *Attorney, Agent, or Firm* — Foley & Lardner LLP

(57) ABSTRACT

Provided is a compound having an antagonistic action on an NMDA receptor containing the NR2B subunit, and is useful as a prophylactic or therapeutic agent for major depression, bipolar disorder, migraine, pain, peripheral symptoms of dementia and the like. A compound represented by the formula (I):

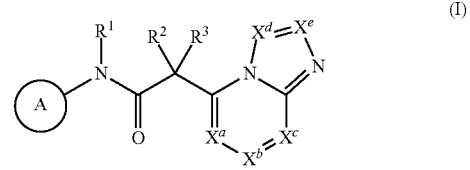

wherein each symbol is as described in the DESCRIPTION, (excluding N-(4-bromo-3-(1H-1,2,4-triazol-5-yl)thiophen-2-yl)-2-(imidazo[1,2-a]pyridin-5-yl)acetamide) or a salt thereof.

6 Claims, No Drawings

HETEROCYCLIC COMPOUND

CROSS-REFERENCE TO RELATED APPLICATIONS

This application is a National Stage application of PCT/JP2015/085689, filed Dec. 21, 2015, which claims priority from Japanese application JP 2014-259662, filed Dec. 24, 2014.

TECHNICAL FIELD

The present invention relates to a heterocyclic compound having an antagonistic action on an N-methyl-D-aspartic acid (NMDA) receptor containing the NR2B subunit, and useful as a prophylactic or therapeutic agent for major depression, bipolar disorder, migraine, pain, peripheral symptoms of dementia and the like.

BACKGROUND OF THE INVENTION

The major excitatory neurotransmitter in the central nervous system such as the brain, spinal cord and the like is glutamic acid, and its signal transduction is mediated by N-methyl-D-aspartic acid (NMDA) receptor, gamma-amino-3-hydroxy-5-methyloxazole-4-propionic acid (AMPA)/kainic acid (KA) receptor and metabotropic glutamate receptor. Of these, NMDA receptor is highly permeable to cations including calcium ion and mediate excitatory neurotransmission by depolarizing nerve cells. In addition, calcium flowing into the cell via NMDA receptor functions as a secondary messenger, and causes plastic changes in the nerve function through actions such as changes in the intracellular phosphorylation signal, regulation of transcription and translation of the gene, and the like. Thus, NMDA receptor plays an important role in the functional regulation of central nervous system.

The NMDA receptor is a receptor composed of a tetramer in which 2 to 3 subunits from among NR1, NR2A, NR2B, NR2C, NR2D, NR3A, NR3B subunits are associated, and, to have the function of a receptor responsible for excitatory neurotransmission, the presence of the NR1 subunit is essential. Since the NR1 subunit is contained in all NMDA receptors having the function, it is widely distributed in the central nervous system; however, the distribution and the timing of expression of the NR2 subunit are different for each subunit. For example, NR2A and NR2C subunits are detected only immediately before birth, whereas NR2B and NR2D subunits are observed from an early stage in embryonic development. For example, while the NR2A subunit is widely distributed in the brain, the NR2B subunit is locally expressed in the forebrain and the NR2C subunit is locally expressed in the cerebellum (non-patent document 1).

An NMDA receptor containing the NR2B subunit, which is the target in the present invention, is highly expressed in the cerebral cortex (particularly the second or third layer), hippocampus, amygdala, ventral nucleus of thalamus, and olfactory bulb in the brain of adult rodents. The NMDA receptor is confined to the dorsal horn of the spinal cord (particularly the second layer) in the spinal cord (non-patent document 2). Moreover, in a single cell, the NMDA receptor containing the NR2B subunit is most highly expressed in postsynaptic density and the expression is also found in the extrasynaptic region (non-patent document 3). This suggests that an NMDA receptor containing the NR2B subunit functions widely in the brain and is effective for the prophylaxis or treatment of central diseases.

Non-patent document 4 discloses the following compound used for the evaluation of central migration property.

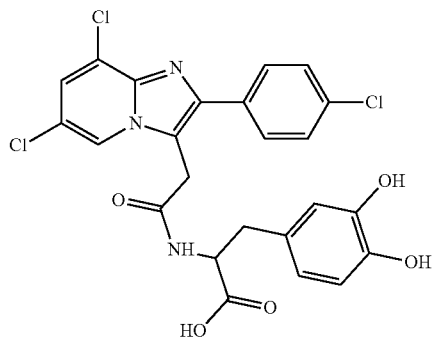

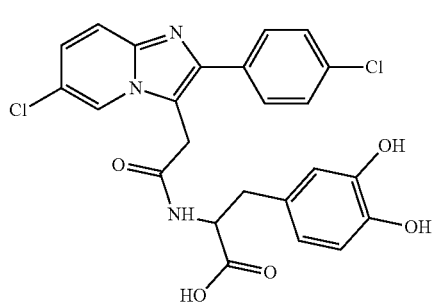

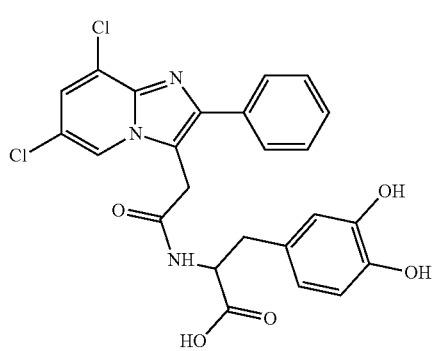

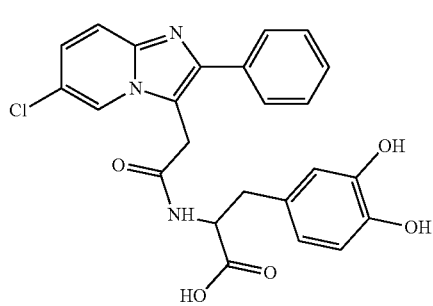

5

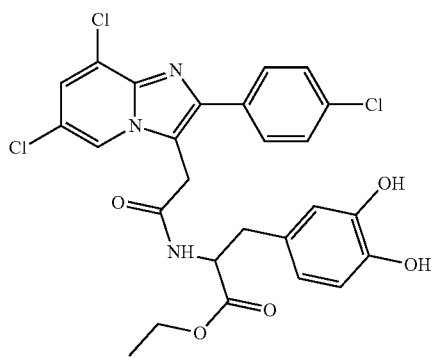

6

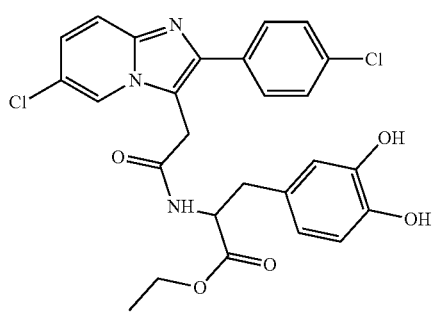

7

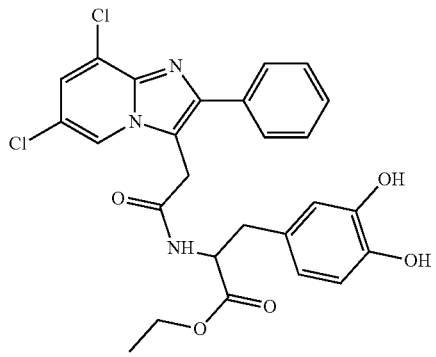

8

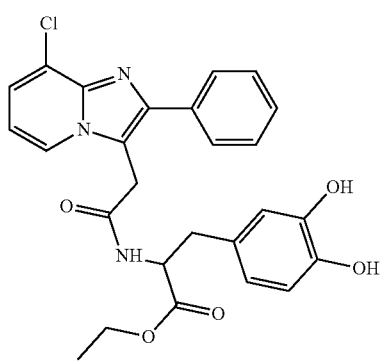

9

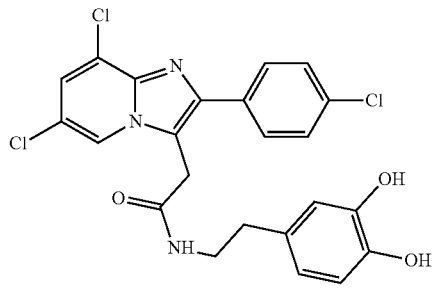

10

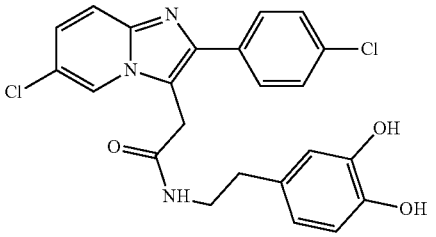

11

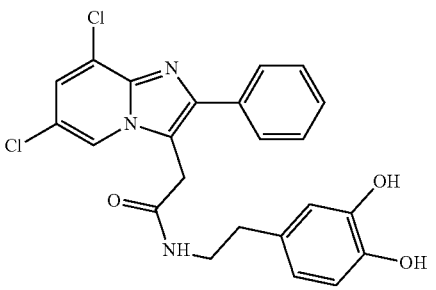

12

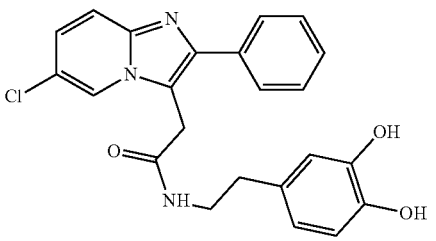

Patent document 1 discloses the following compound having a c-Jun N-terminus kinase (JNK) inhibitory action, and useful for the prophylaxis or treatment of neurodegenerative disease (Alzheimer's disease, Parkinson's disease, Down's disease, MCI, ALS etc.), pain and the like.

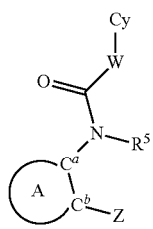

wherein each symbol is as defined in the document.

Patent document 2 discloses the following compound having a JNK inhibitory action, and useful for the prophylaxis or treatment of neurodegenerative disease (Alzheimer's disease, Huntington chorea, Parkinson's disease, epilepsy, amyotrophic lateral sclerosis, peripheral nerve disorders) and the like.

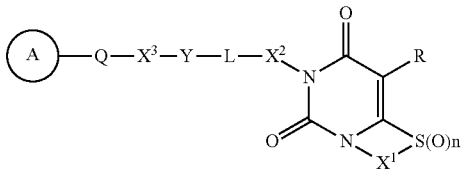

wherein each symbol is as defined in the document.

Patent document 3 discloses the following compound useful as a photosensitive material of silver halide photographs.

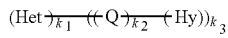

wherein each symbol is as defined in the document.

Patent document 4 discloses the following compound having an adhesion molecule expression inhibitory action and useful for the prophylaxis or treatment of diabetic nephropathy, rejection in organ transplantation, autoimmune disease and the like.

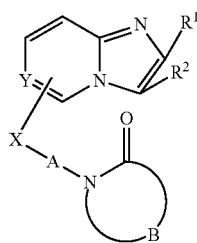

wherein each symbol is as defined in the document.

DOCUMENT LIST

Patent Documents patent document 1: WO 2010091310
patent document 2: JP2004161716
patent document 3: JP08137043
patent document 4: WO 9535296

Non-Patent Document non-patent document 1: Neuron, vol. 12, pp. 529-540, 1994
non-patent document 2: the Journal of Comparative Neurology (J. Comp. Neurol.), vol. 338, pp, 377-390, 1993
non-patent document 3: Molecular Cells (Mol. Cells), vol. 7, pp. 64-71, 1997
non-patent document 4: International Journal of Nanomedicine (2012), 7, 3211-3219

SUMMARY OF THE INVENTION

Problems to be Solved by the Invention

An object of the present invention is to provide a heterocyclic compound having an antagonistic action on NMDA receptor containing the NR2B subunit, and useful as a prophylactic or therapeutic agent for major depression, bipolar disorder, migraine, pain, peripheral symptoms of dementia and the like, and a medicament containing the same.

Means of Solving the Problems

The present inventors have conducted intensive studies in an attempt to solve the above-mentioned problem, and found that a compound represented by the following formula (I) has a superior antagonistic action on an NMDA receptor containing the NR2B subunit, which resulted in the completion of the present invention.

Therefore, the present invention provides the following.
[1] A compound represented by the formula (I):

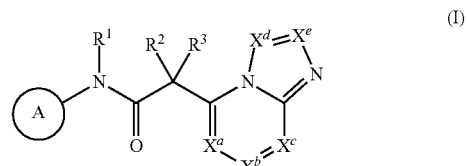

wherein
ring A is an optionally further substituted ring;
$R^1$ is a hydrogen atom or a substituent;
$R^2$ and $R^3$ are each independently a hydrogen atom, an optionally substituted $C_{1-6}$ alkyl group or an optionally substituted $C_{3-10}$ cycloalkyl group;
$X^a$ is $CR^a$ or N;
$X^b$ is $CR^b$ Or N;
$X^c$ is $CR^c$ or N;
$X^d$ is $CR^d$ or N;
$X^e$ is $CR^e$ or N; and
$R^a$, $R^b$, $R^c$, $R^d$ and $R^e$ are each independently a hydrogen atom or a substituent
(excluding N-(4-bromo-3-(1H-1,2,4-triazol-5-yl)thiophen-2-yl)-2-(imidazo[1,2-a]pyridin-5-yl)acetamide)
or a salt thereof (sometimes to be abbreviated as "compound (I)" in the present specification);
[2] the compound of [1], wherein
ring A is a $C_{6-14}$ aromatic hydrocarbon ring, a 5- to 14-membered aromatic heterocycle, a $C_{3-10}$ cycloalkane, or a 3- to 14-membered non-aromatic heterocycle, each of which is optionally further substituted by 1 to 3 substituents selected from
(1) a halogen atom,
(2) a cyano group,
(3) an optionally substituted $C_{1-6}$ alkyl group,
(4) an optionally substituted $C_{1-6}$ alkoxy group,
(5) an optionally substituted $C_{3-10}$ cycloalkyl group,
(6) an optionally substituted carbamoyl group,
(7) an optionally substituted sulfanyl group,
(8) an optionally substituted $C_{6-14}$ aryloxy group,
(9) an optionally substituted 3- to 14-membered non-aromatic heterocyclyloxy group,
(10) an optionally substituted $C_{3-10}$ cycloalkyloxy group, and
(11) an optionally substituted 3- to 14-membered nonaromatic heterocyclic group;
$R^1$ is a hydrogen atom, an optionally substituted $C_{1-6}$ alkyl group, or an optionally substituted $C_{3-10}$ cycloalkyl group;
$R^2$ and $R^3$ are each independently a hydrogen atom, or an optionally substituted $C_{1-6}$ alkyl group;

$X^a$ is $CR^a$;
$X^c$ is $CR^c$;
$R^a$ is a hydrogen atom, a halogen atom, an optionally substituted $C_{1-6}$ alkyl group, or an optionally substituted $C_{1-6}$ alkoxy group;
$R^b$ and $R^c$ are each independently a hydrogen atom, a halogen atom, or an optionally substituted $C_{1-6}$ alkyl group;
$R^d$ is a hydrogen atom; and
$R^e$ is a hydrogen atom or an optionally substituted $C_{1-6}$ alkyl group,
or a salt thereof;
[3] the compound of [1] or [2], wherein ring A is a $C_{6-14}$ aromatic hydrocarbon ring, a 5- to 14-membered aromatic heterocycle, a $C_{3-10}$ cycloalkane, or a 3- to 14-membered non-aromatic heterocycle, each of which is optionally further substituted by 1 to 3 substituents selected from
(1) a halogen atom,
(2) a cyano group,
(3) a $C_{1-6}$ alkyl group optionally substituted by 1 to 3 halogen atoms,
(4) a $C_{1-6}$ alkoxy group optionally substituted by 1 to 3 halogen atoms,
(5) a $C_{3-10}$ cycloalkyl group,
(6) a carbamoyl group optionally mono- or di-substituted by a $C_{1-6}$ alkyl group,
(7) a sulfanyl group optionally substituted by 1 to 6 halogen atoms,
(8) a $C_{6-14}$ aryloxy group,
(9) a 3- to 14-membered non-aromatic heterocyclyloxy group,
(10) a $C_{3-10}$ cycloalkyloxy group, and
(11) a 3- to 14-membered nonaromatic heterocyclic group optionally substituted by 1 to 3 halogen atoms;
$R^1$ is (i) a hydrogen atom, or (ii) a $C_{1-6}$ alkyl group optionally substituted by 1 to 3 substituents selected from a cyano group, a hydroxy group and a $C_{6-14}$ aryl group;
$R^2$ and $R^3$ are each independently a hydrogen atom, or a $C_{1-6}$ alkyl group;
$X^a$ is $CR^a$;
$X^c$ is $CR^c$;
$R^a$ is a hydrogen atom, a halogen atom, $C_{1-6}$ alkyl group, or a $C_{1-6}$ alkoxy group;
$R^b$ and $R^c$ are each independently a hydrogen atom, a halogen atom, or a $C_{1-6}$ alkyl group;
$R^d$ is a hydrogen atom; and
$R^e$ is a hydrogen atom or a $C_{1-6}$ alkyl group,
or a salt thereof;
[4] the compound of [1], wherein ring A is an optionally further substituted $C_{6-14}$ aromatic hydrocarbon ring, or a salt thereof;
[5] the compound of [1] or [4], wherein ring A is an optionally further substituted benzene ring, or a salt thereof;
[6] the compound of any of [1], [4] and [5], wherein ring A is a benzene ring optionally further substituted by 1 to 3 substituents selected from
(1) a halogen atom,
(2) a cyano group,
(3) an optionally substituted $C_{1-6}$ alkyl group,
(4) an optionally substituted $C_{1-6}$ alkoxy group,
(5) an optionally substituted $C_{3-10}$ cycloalkyl group,
(6) an optionally substituted carbamoyl group,
(7) an optionally substituted sulfanyl group,
(8) an optionally substituted $C_{6-14}$ aryloxy group,
(9) an optionally substituted 3- to 14-membered non-aromatic heterocyclyloxy group,
(10) an optionally substituted $C_{3-10}$ cycloalkyloxy group,
(11) an optionally substituted 3- to 14-membered nonaromatic heterocyclic group, and
(12) an optionally substituted 5- to 14-membered aromatic heterocyclic group;
$R^1$ is a hydrogen atom, an optionally substituted $C_{1-6}$ alkyl group, or an optionally substituted $C_{3-10}$ cycloalkyl group;
$R^2$ and $R^3$ are each independently a hydrogen atom, or an optionally substituted $C_{1-6}$ alkyl group;
$X^a$ is $CR^a$;
$X^c$ is $CR^c$;
$R^a$ is a hydrogen atom, a halogen atom, an optionally substituted $C_{1-6}$ alkyl group, or an optionally substituted $C_{1-6}$ alkoxy group;
$R^b$ and $R^c$ are each independently a hydrogen atom, a halogen atom, or an optionally substituted $C_{1-6}$ alkyl group;
$R^d$ is a hydrogen atom; and
$R^e$ is a hydrogen atom or an optionally substituted $C_{1-6}$ alkyl group,
or a salt thereof;
[7] the compound of any of [1], [4]-[6], wherein ring A is a benzene ring optionally further substituted by 1 to 3 substituents selected from
(1) a halogen atom,
(2) a cyano group,
(3) a $C_{1-6}$ alkyl group optionally substituted by 1 to 3 halogen atoms,
(4) a $C_{1-6}$ alkoxy group optionally substituted by 1 to 3 halogen atoms,
(5) a $C_{3-10}$ cycloalkyl group,
(6) a carbamoyl group optionally mono- or di-substituted by a $C_{1-6}$ alkyl group,
(7) a sulfanyl group optionally substituted by 1 to 6 halogen atoms,
(8) a $C_{6-14}$ aryloxy group,
(9) a 3- to 14-membered non-aromatic heterocyclyloxy group,
(10) a $C_{3-10}$ cycloalkyloxy group,
(11) a 3- to 14-membered nonaromatic heterocyclic group optionally substituted by 1 to 3 halogen atoms, and
(12) a 5- to 14-membered aromatic heterocyclic group; $R^1$ is (i) a hydrogen atom, or (ii) a $C_{1-6}$ alkyl group optionally substituted 1 to 3 substituents selected from a cyano group, a hydroxy group and a $C_{6-14}$ aryl group;
$R^2$ and $R^3$ are each independently a hydrogen atom, or a $C_{1-6}$ alkyl group;
$X^a$ is $CR^a$;
$X^c$ is $CR^c$;
$R^a$ is a hydrogen atom, a halogen atom, a $C_{1-6}$ alkyl group, or a $C_{1-6}$ alkoxy group;
$R^b$ and $R^c$ are each independently a hydrogen atom, a halogen atom, or a $C_{1-6}$ alkyl group;
$R^d$ is a hydrogen atom; and
$R^e$ is a hydrogen atom or a $C_{1-6}$ alkyl group,
or a salt thereof;
[8] the compound of any of [1]-[7], wherein ring A is a benzene ring optionally further substituted by 1 to 3 substituents selected from
(1) a $C_{1-6}$ alkoxy group optionally substituted by 1 to 3 halogen atoms,
(2) a $C_{1-6}$ alkyl group optionally substituted by 1 to 3 halogen atoms,
(3) a halogen atom, and
(4) a $C_{3-10}$ cycloalkyl group;
$R^1$, $R^2$ and $R^3$ are each a hydrogen atom;
$X^a$ is $CR^a$;
$X^b$ is $CR^b$;

$X^c$ is $CR^c$;
$X^d$ is $CR^d$;
$X^e$ is $CR^e$;
$R^a$ is a hydrogen atom, a $C_{1-6}$ alkyl group or a $C_{1-6}$ alkoxy group; and
$R^b$, $R^c$, $R^d$ and $R^e$ are each a hydrogen atom,
or a salt thereof;

[9] 2-(imidazo[1,2-a]pyridin-5-yl)-N-(4-(trifluoromethyl)phenyl)acetamide or a salt thereof;

[10] 2-(imidazo[1,2-a]pyridin-5-yl)-N-(4-methoxyphenyl)acetamide or a salt thereof;

[11] N-(3-fluoro-4-methoxyphenyl)-2-(imidazo[1,2-a]pyridin-5-yl)acetamide or a salt thereof;

[12] a medicament comprising the compound of any of [1]-[11], or a salt thereof;

[13] the medicament of [12], which is an antagonist of an NMDA receptor containing the NR2B subunit;

[14] the medicament of [12], which is a prophylactic or therapeutic agent for major depression, bipolar disorder, migraine, pain, or peripheral symptoms of dementia;

[15] the compound of any of [1]-[11] or a salt thereof, which is used for the prophylaxis or treatment of major depression, bipolar disorder, migraine, pain, or peripheral symptoms of dementia;

[16] a method of inhibiting an NMDA receptor containing the NR2B subunit in a mammal, comprising administering an effective amount of the compound of any of [1]-[11] or a salt thereof to the mammal;

[17] a method for the prophylaxis or treatment of major depression, bipolar disorder, migraine, pain, or peripheral symptoms of dementia in a mammal, comprising administering an effective amount of the compound of any of [1]-[11] or a salt thereof to the mammal; and

[18] use of the compound of any of [1]-[11] or a salt thereof for the manufacture of a prophylactic or therapeutic agent for major depression, bipolar disorder, migraine, pain, or peripheral symptoms of dementia.

Effect of the Invention

The present invention provides a heterocyclic compound having an antagonistic action on an NMDA receptor containing the NR2B subunit and useful as a prophylactic or therapeutic agent for major depression, bipolar disorder, migraine, pain, peripheral symptoms of dementia and the like, and a medicament containing the same.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms.

Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,

(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl)($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbonsulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxycarbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl)($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".
Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl)

In the present specification, examples of the "hydrocarbocycle" include a $C_{6-14}$ aromatic hydrocarbocycle, $C_{3-10}$ cycloalkane and $C_{3-10}$ cycloalkene.

In the present specification, examples of the "$C_{6-14}$ aromatic hydrocarbocycle" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "ring" of the "optionally substituted ring" include the above-mentioned "hydrocarbon ring" and "heterocycle", and examples of the substituent thereof include the above-mentioned "substituent".

The definition of each symbol in the formula (I) is described in detail below.

Ring A is an optionally further substituted ring.

The "ring" of the "optionally further substituted ring" for ring A is a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring), a 3- to 14-membered non-aromatic heterocycle (e.g., dihydrobenzofuran ring) or the like.

The above-mentioned "ring" is preferably a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring) or a $C_{3-10}$ cycloalkane (e.g., cyclohexane ring), more preferably, a $C_{6-14}$ aromatic hydrocarbon ring (e.g., benzene ring) or a 5- to 14-membered aromatic heterocycle (e.g., pyrazole ring, thiadiazole ring, pyridine ring, pyrimidine ring, pyrazine ring, benzothiophene ring, benzoxazole ring), further preferably a benzene ring or a 5- or 6-membered aromatic heterocycle (e.g., pyrazole ring, thiadiazole ring, pyridine ring, pyrimidine ring, pyrazine ring), most preferably a benzene ring.

The "ring" of the "optionally further substituted ring" for ring A is optionally further substituted by 1-5 (preferably 1-3, more preferably 1 or 2) substituents other than —C($R^2$)($R^3$)—C(=O)—N($R^1$)— group at substitutable position(s). Examples of such substituent include the above-mentioned "substituent", which are preferably, (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl), more preferably, (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy) and (11) an optionally substituted 3- to 14-membered non-aromatic heterocyclic group (e.g., azetidinyl), further preferably, (1) a halogen atom (e.g., fluorine atom, bromine atom, chlorine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-5 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy) and (11) a 3- to 14-membered nonaromatic heterocyclic group (e.g., azetidinyl) optionally substituted by 1 to 3 halogen atoms (e.g., fluorine atom), particularly preferably, (1) a halogen atom (e.g., fluorine atom, chlorine atom, iodine atom), (2) a $C_{1-6}$ alkyl group (e.g., methyl, ethyl, propyl) optionally substituted by 1 to 3 halogen atoms (e.g., fluorine atom), (3) a $C_{1-6}$ alkoxy group (e.g., methoxy, ethoxy) optionally substituted by 1 to 3 halogen atoms (e.g., fluorine atom) and (4) a $C_{3-10}$ cycloalkyl group (e.g., cyclopropyl).

Ring A is preferably a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl).

In another embodiment of the present invention, ring A is preferably a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring) or a $C_{3-10}$ cycloalkane (e.g., cyclohexane ring), each of which is optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl).

In another embodiment of the present invention, ring A is preferably (i) a $C_{6-14}$ aromatic hydrocarbon ring (e.g., benzene ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl), or (ii) a 5- to 14-membered aromatic heterocycle (e.g., pyrazole ring, thiadiazole ring, pyridine ring, pyrimidine ring, pyrazine ring, benzothiophene ring, benzoxazole ring) optionally further substituted by 1-5 (preferably 1-3, more preferably 1 or 2) substituents selected from (1) a halogen atom (e.g., fluorine atom, chlorine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy) and (11) an optionally substituted 3- to 14-membered nonaromatic heterocyclic group (e.g., azetidinyl).

Ring A is more preferably, (A) a $C_{6-14}$ aromatic hydrocarbon ring (e.g., benzene ring) optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-5 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy), (11) an optionally substituted 5- to 14-membered aromatic heterocyclic group (e.g., thienyl), and (12) a 3- to 14-membered nonaromatic heterocyclic group (e.g., azetidinyl) optionally substituted by 1 to 3 halogen atoms (e.g., fluorine atom), (B) a 5- to 14-membered aromatic heterocycle (e.g., pyrazole ring, thiadiazole ring, pyridine ring, pyrimidine ring, pyrazine ring, benzothiophene ring, benzoxazole ring) optionally further substituted by 1-5 (preferably 1-3, more preferably 1 or 2) substituents selected from (1) a $C_{1-6}$ alkyl group (e.g., methyl, ethyl) optionally substituted by 1 to 3 halogen atoms (e.g., fluorine atom), (2) a $C_{1-6}$ alkoxy group (e.g., methoxy) optionally substituted by 1 to 3 halogen atoms (e.g., fluorine atom) and (3) a $C_{3-10}$ cycloalkyl group (e.g., cyclopropyl), (C) a $C_{3-10}$ cycloalkane (e.g., cyclohexane ring) optionally further substituted by 1-5 (preferably 1-3, more preferably 1 or 2) substituents selected from a $C_{1-6}$ alkyl group (e.g., methyl) optionally substituted by 1 to 3 halogen atoms (e.g., fluorine atom), or (D) a 3- to 14-membered non-aromatic heterocycle (e.g., dihydrobenzofuran ring).

Ring A is further preferably (A) a $C_{6-14}$ aromatic hydrocarbon ring (e.g., benzene ring) optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-5 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy), (11) an optionally substituted 5- to 14-membered aromatic heterocyclic group (e.g., thienyl) and (12) a 3- to 14-membered nonaromatic heterocyclic group (e.g., azetidinyl) optionally substituted by 1 to 3 halogen atoms (e.g., fluorine atom) or (B) a 5- to 14-membered aromatic heterocycle (e.g., pyrazole ring, thiadiazole ring, pyridine ring, pyrimidine ring, pyrazine ring, benzothiophene ring, benzoxazole ring) optionally further substituted by 1-5 (preferably 1-3, more preferably 1 or 2) substituents selected from (1) a $C_{1-6}$ alkyl group (e.g., methyl, ethyl) optionally substituted by 1 to 3 halogen atoms (e.g., fluorine atom), (2) a $C_{1-6}$ alkoxy group (e.g., methoxy) optionally substituted by 1 to 3 halogen atoms (e.g., fluorine atom) and (3) a $C_{3-10}$ cycloalkyl group (e.g., cyclopropyl).

Ring A is particularly preferably a $C_{6-14}$ aromatic hydrocarbon ring (e.g., benzene ring) optionally further substituted by 1-5 (preferably 1-3, more preferably 1 or 2) substituents selected from (1) a halogen atom (e.g., fluorine atom, chlorine atom, bromine atom, iodine atom), (2) a $C_{1-6}$ alkyl group (e.g., methyl, ethyl, propyl) optionally substituted by 1 to 3 halogen atoms (e.g., fluorine atom), (3) a $C_{1-6}$ alkoxy group (e.g., methoxy, ethoxy) optionally substituted by 1 to 3 halogen atoms (e.g., fluorine atom) and (4) a $C_{3-10}$ cycloalkyl group (e.g., cyclopropyl).

In a yet another embodiment of the present invention, ring A is preferably, a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy) and (11) an optionally substituted 3- to 14-membered non-aromatic heterocyclic group (e.g., azetidinyl), more preferably, a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, bromine atom, chlorine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-6 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy) and (11) a 3- to 14-membered nonaromatic heterocyclic group (e.g., azetidinyl) optionally substituted by 1 to 3 halogen atoms (e.g., fluorine atom).

In a yet another embodiment of the present invention, ring A is preferably, a benzene ring optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl), more preferably, a benzene ring optionally further substituted by 1-5 (preferably 1-3, more preferably 1 or 2) substituents selected from (1) a halogen atom (e.g., fluorine atom, bromine atom, chlorine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-6 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy), (11) a 5- to 14-membered aromatic heterocyclic group (e.g., thienyl) and (12) a 3- to 14-membered nonaromatic heterocyclic group (e.g., azetidinyl) optionally substituted by 1 to 3 halogen atoms (e.g., fluorine atom).

In a yet another embodiment of the present invention, ring A is preferably a benzene ring optionally further substituted by 1-5 (preferably 1-3, more preferably 1 or 2) substituents selected from (1) a $C_{1-6}$ alkoxy group (e.g., methoxy, ethoxy) optionally substituted by 1 to 3 halogen atoms (e.g., fluorine atom), (2) a $C_{1-6}$ alkyl group (e.g., methyl, ethyl, propyl) optionally substituted by 1 to 3 halogen atoms (e.g., fluorine atom), (3) a halogen atom (e.g., fluorine atom, chlorine atom, bromine atom, iodine atom) and (4) a $C_{3-10}$ cycloalkyl group (e.g., cyclopropyl).

In a yet another embodiment of the present invention, ring A is preferably an optionally further substituted $C_{6-14}$ aromatic hydrocarbon ring (e.g., benzene ring), more preferably, an optionally further substituted benzene ring.

$R^1$ is a hydrogen atom or a substituent.

Examples of the "substituent" for $R^1$ include the above-mentioned "substituent", and an optionally substituted $C_{1-6}$ alkyl group (e.g., methyl, ethyl, isopropyl) or an optionally substituted $C_{3-10}$ cycloalkyl group is preferable, and a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl) is more preferable.

$R^1$ is preferably a hydrogen atom, an optionally substituted $C_{1-6}$ alkyl group (e.g., methyl, ethyl, isopropyl) or an optionally substituted $C_{3-10}$ cycloalkyl group, more preferably, (i) a hydrogen atom, or (ii) a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl), further preferably, a hydrogen atom.

$R^2$ and $R^3$ are each independently a hydrogen atom, an optionally substituted $C_{1-6}$ alkyl group or an optionally substituted $C_{3-10}$ cycloalkyl group.

$R^2$ and $R^3$ are each preferably a hydrogen atom.

In another embodiment of the present invention, $R^2$ and $R^3$ are preferably each independently a hydrogen atom, or an optionally substituted $C_{1-6}$ alkyl group (e.g., methyl), more preferably, each is independently a hydrogen atom or a $C_{1-6}$ alkyl group (e.g., methyl), more preferably, each is a hydrogen atom.

$X^a$ is $CR^a$ or N, $X^b$ is $CR^b$ or N, $X^c$ is $CR^c$ or N, $X^d$ is $CR^d$ or N, $X^e$ is $CR^e$ or N, $R^a$, $R^b$, $R^c$, $R^d$ and $R^e$ are each independently a hydrogen atom or a substituent.

Examples of the "substituent" for $R^a$, $R^b$, $R^c$, $R^d$ or $R^e$ include the above-mentioned "substituent", and a halogen atom (e.g., fluorine atom, chlorine atom), an optionally substituted $C_{1-6}$ alkyl group (e.g., methyl, ethyl) or an optionally substituted $C_{1-6}$ alkoxy group (e.g., methoxy) is preferable, and a halogen atom (e.g., fluorine atom), a $C_{1-6}$ alkyl group (e.g., methyl, ethyl) or a $C_{1-6}$ alkoxy group (e.g., methoxy) is more preferable.

$X^a$ is preferably $CR^a$ ($R^a$ is a hydrogen atom or a halogen atom (e.g., fluorine atom)), more preferably, $CR^a$ ($R^a$ is a hydrogen atom).

In another embodiment of the present invention, $X^a$ is preferably $CR^a$ ($R^a$ is a hydrogen atom, a halogen atom (e.g., fluorine atom, chlorine atom), an optionally substituted $C_{1-6}$ alkyl group (e.g., methyl, ethyl) or an optionally substituted $C_{1-6}$ alkoxy group (e.g., methoxy)), more preferably, $CR^a$ ($R^a$ is a hydrogen atom, a halogen atom (e.g., fluorine atom, chlorine atom), a $C_{1-6}$ alkyl group (e.g., methyl, ethyl) or a $C_{1-6}$ alkoxy group (e.g., methoxy)), further more preferably, $CR^a$ ($R^a$ is a hydrogen atom, a $C_{1-6}$ alkyl group (e.g., methyl, ethyl) or a $C_{1-6}$ alkoxy group (e.g., methoxy)).

$X^b$ is preferably $CR^b$ ($R^b$ is a hydrogen atom or an optionally substituted $C_{1-6}$ alkyl group (e.g., methyl)) or N, more preferably, $CR^b$ ($R^b$ is a hydrogen atom or a $C_{1-6}$ alkyl group (e.g., methyl)) or N, further preferably, $CR^b$ ($R^b$ is a hydrogen atom).

In another embodiment of the present invention, $X^b$ is preferably $CR^b$ ($R^b$ is a hydrogen atom, a halogen atom (e.g., fluorine atom) or an optionally substituted $C_{1-6}$ alkyl group (e.g., methyl)) or N, more preferably, $CR^b$ ($R^b$ is a hydrogen atom, a halogen atom (e.g., fluorine atom) or a $C_{1-6}$ alkyl group (e.g., methyl)) or N, further preferably, $CR^b$ ($R^b$ is a hydrogen atom).

$X^c$ is preferably $CR^c$ ($R^c$ is a hydrogen atom or an optionally substituted $C_{1-6}$ alkyl group (e.g., methyl)), more preferably, $CR^c$ ($R^c$ is a hydrogen atom or a $C_{1-6}$ alkyl group (e.g., methyl)), further preferably, $CR^c$ ($R^c$ is a hydrogen atom).

In another embodiment of the present invention, $X^c$ is preferably $CR^c$ ($R^c$ is a hydrogen atom, a halogen atom (e.g., fluorine atom) or an optionally substituted $C_{1-6}$ alkyl group (e.g., methyl)), more preferably, $CR^c$ ($R^c$ is a hydrogen atom, a halogen atom (e.g., fluorine atom) or a $C_{1-6}$ alkyl group (e.g., methyl)), further preferably, $CR^c$ ($R^c$ is a hydrogen atom).

$X^d$ is preferably $CR^d$ ($R^d$ is a hydrogen atom or an optionally substituted $C_{1-6}$ alkyl group (e.g., methyl)) or N, more preferably, $CR^d$ ($R^d$ is a hydrogen atom or $C_{1-6}$ alkyl group (e.g., methyl)) or N, further preferably, $CR^d$ ($R^d$ is a hydrogen atom).

In another embodiment of the present invention, $X^d$ is preferably $CR^d$ ($R^d$ is a hydrogen atom) or N, more preferably, $CR^d$ ($R^d$ is a hydrogen atom).

$X^e$ is preferably $CR^e$ ($R^e$ is a hydrogen atom or an optionally substituted $C_{1-6}$ alkyl group (e.g., methyl)) or N, more preferably, $CR^e$ ($R^e$ is a hydrogen atom or $C_{1-6}$ alkyl group (e.g., methyl)) or N, further preferably, $CR^e$ ($R^e$ is a hydrogen atom).

In another embodiment of the present invention, $X^e$ is preferably $CR^e$ ($R^e$ is a hydrogen atom or an optionally substituted $C_{1-6}$ alkyl group (e.g., methyl)) or N, more preferably, $CR^e$ ($R^e$ is a hydrogen atom or $C_{1-6}$ alkyl group (e.g., methyl)) or N, further preferably, $CR^e$ ($R^e$ is a hydrogen atom)

Preferable examples of compound (I) include the following compounds.

[Compound A]

Compound (I) wherein ring A is a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, chlorine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl);

$R^1$ is (i) a hydrogen atom, or (ii) a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl);

$R^2$ and $R^3$ are each a hydrogen atom;

$X^a$ is $CR^a$ ($R^a$ is a hydrogen atom or a halogen atom (e.g., fluorine atom));

$X^b$ is $CR^b$ ($R^b$ is a hydrogen atom or an optionally substituted $C_{1-6}$ alkyl group (e.g., methyl)) or N;

$X^c$ is $CR^c$ ($R^c$ is a hydrogen atom or an optionally substituted $C_{1-6}$ alkyl group (e.g., methyl));

$X^d$ is $CR^d$ ($R^d$ is a hydrogen atom or an optionally substituted $C_{1-6}$ alkyl group (e.g., methyl)) or N; and $X^e$ is $CR^e$ ($R^e$ is a hydrogen atom or an optionally substituted $C_{1-6}$ alkyl group (e.g., methyl)) or N.

[Compound B]

Compound (I) wherein ring A is (A) a $C_{6-14}$ aromatic hydrocarbon ring (e.g., benzene ring) optionally further substituted by 1-5 (preferably 1-3, more preferably 1 or 2) substituents selected from (1) a halogen atom (e.g., fluorine atom, chlorine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-5 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy), (11) an optionally substituted 5- to 14-membered aromatic heterocyclic group (e.g., thienyl), and (12) a 3- to 14-membered nonaromatic heterocyclic group (e.g., azetidinyl) optionally substituted by 1 to 3 halogen atoms (e.g., fluorine atom), (B) a 5- to 14-membered aromatic heterocycle (e.g., pyrazole ring, thiadiazole ring, pyridine ring, pyrimidine ring, pyrazine ring, benzothiophene ring, benzoxazole ring) optionally further substituted by 1-5 (preferably 1-3, more preferably 1 or 2) substituents selected from (1) a $C_{1-6}$ alkyl group (e.g., methyl) optionally substituted by 1 to 3 halogen atoms (e.g., fluorine atom), (2) a $C_{1-6}$ alkoxy group (e.g., methoxy) optionally substituted by 1 to 3 halogen atoms (e.g., fluorine atom) and (3) a $C_{3-10}$ cycloalkyl group (e.g., cyclopropyl), (C) a $C_{3-10}$ cycloalkane (e.g., cyclohexane ring) optionally further substituted by 1-5 (preferably 1-3, more preferably 1 or 2) substituents selected from a $C_{1-6}$ alkyl group (e.g., methyl) optionally substituted by 1 to 3 halogen atoms (e.g., fluorine atom) or (D) a 3- to 14-membered non-aromatic heterocycle (e.g., dihydrobenzofuran ring);

$R^1$ is (i) a hydrogen atom, or (ii) a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl);

$R^2$ and $R^3$ are each a hydrogen atom;

$X^a$ is $CR^a$ ($R^a$ is a hydrogen atom or a halogen atom (e.g., fluorine atom));

$X^b$ is $CR^b$ ($R^b$ is a hydrogen atom or an optionally substituted $C_{1-6}$ alkyl group (e.g., methyl)) or N;

$X^c$ is $CR^c$ ($R^c$ is a hydrogen atom or an optionally substituted $C_{1-6}$ alkyl group (e.g., methyl));

$X^d$ is $CR^d$ ($R^d$ is a hydrogen atom or an optionally substituted $C_{1-6}$ alkyl group (e.g., methyl)) or N; and $X^e$ is $CR^e$ ($R^e$ is a hydrogen atom or an optionally substituted $C_{1-6}$ alkyl group (e.g., methyl)) or N.

[Compound C]

Compound (I) wherein ring A is a $C_{6-14}$ aromatic hydrocarbon ring (e.g., benzene ring) optionally further substituted by 1-5 (preferably 1-3, more preferably 1 or 2) substituents selected from (1) a halogen atom (e.g., fluorine atom, chlorine atom, iodine atom), (2) a $C_{1-6}$ alkyl group (e.g., methyl, ethyl, propyl) optionally substituted by 1 to 3 halogen atoms (e.g., fluorine atom), (3) a $C_{1-6}$ alkoxy group (e.g., methoxy, ethoxy) optionally substituted by 1 to 3 halogen atoms (e.g., fluorine atom) and (4) a $C_{3-10}$ cycloalkyl group (e.g., cyclopropyl);

$R^1$ is a hydrogen atom;

$R^2$ and $R^3$ are each a hydrogen atom;

$X^a$ is $CR^a$ ($R^a$ is a hydrogen atom);

$X^b$ is $CR^b$ ($R^b$ is a hydrogen atom);

$X^c$ is $CR^c$ ($R^c$ is a hydrogen atom);

$X^d$ is $CR^d$ ($R^d$ is a hydrogen atom); and $X^e$ is $CR^e$ ($R^e$ is a hydrogen atom).

[Compound D]

Compound (I) wherein ring A is a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, pyrazine ring, benzothiophene ring, benzoxazole ring), a $C_{3-10}$ cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy) and (11) an optionally substituted 3- to 14-membered non-aromatic heterocyclic group (e.g., azetidinyl);

$R^1$ is a hydrogen atom, an optionally substituted $C_{1-6}$ alkyl group (e.g., methyl, ethyl, isopropyl) or an optionally substituted $C_{3-10}$ cycloalkyl group;

$R^2$ and $R^3$ are each independently a hydrogen atom, or an optionally substituted $C_{1-6}$ alkyl group (e.g., methyl);

$X^a$ is $CR^a$;

$X^c$ is $CR^c$;

$R^a$ is a hydrogen atom, a halogen atom (e.g., fluorine atom, chlorine atom), an optionally substituted $C_{1-6}$ alkyl group (e.g., methyl, ethyl) or an optionally substituted $C_{1-6}$ alkoxy group (e.g., methoxy);

$R^d$ is a hydrogen atom; and $R^e$ is a hydrogen atom or an optionally substituted $C_{1-6}$ alkyl group (e.g., methyl).

[Compound E]

Compound (I) wherein ring A is a $C_{6-14}$ aromatic hydrocarbon ring (e.g., benzene ring), a 5- to 14-membered aromatic heterocycle (e.g., pyrazole ring, thiadiazole ring, pyridine ring, pyrimidine ring, a pyrazine ring, benzothiophene ring, benzoxazole ring), a $C_3$-10 cycloalkane (e.g., cyclohexane ring) or a 3- to 14-membered non-aromatic heterocycle (e.g., dihydrobenzofuran ring), each of which is optionally further substituted by 1-5 (preferably 1-3, more preferably 1 or 2) substituents selected from (1) a halogen atom (e.g., fluorine atom, bromine atom, chlorine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-6 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy) and (11) a 3- to 14-membered nonaromatic heterocyclic group (e.g., azetidinyl) optionally substituted by 1 to 3 halogen atoms (e.g., fluorine atom);

$R^1$ is (i) a hydrogen atom, or (ii) a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl);

$R^2$ and $R^3$ are each independently a hydrogen atom or a $C_{1-6}$ alkyl group (e.g., methyl);

$X^a$ is $CR^a$;

$X^c$ is $CR^c$;

$R^a$ is a hydrogen atom, a halogen atom (e.g., fluorine atom, chlorine atom), a $C_{1-6}$ alkyl group (e.g., methyl, ethyl) or a $C_{1-6}$ alkoxy group (e.g., methoxy);

$R^d$ is a hydrogen atom; and $R^e$ is a hydrogen atom or a $C_{1-6}$ alkyl group (e.g., methyl).

[Compound F]

Compound (I) wherein ring A is a benzene ring optionally further substituted by 1-5 (preferably 1-3, more preferably 1 or 2) substituents selected from (1) a halogen atom (e.g., fluorine atom, chlorine atom, bromine atom, iodine atom), (2) a cyano group, (3) an optionally substituted $C_{1-6}$ alkyl group (e.g., methyl, ethyl, propyl, isopropyl, tert-butyl), (4) an optionally substituted $C_{1-6}$ alkoxy group (e.g., methoxy, ethoxy), (5) an optionally substituted $C_{3-10}$ cycloalkyl group (e.g., cyclopropyl), (6) an optionally substituted carbamoyl group, (7) an optionally substituted sulfanyl group, (8) an optionally substituted $C_{6-14}$ aryloxy group (e.g., phenoxy), (9) an optionally substituted 3- to 14-membered non-aromatic heterocyclyloxy group (e.g., oxetanyloxy), (10) an optionally substituted $C_{3-10}$ cycloalkyloxy group (e.g., cyclobutyloxy), (11) an optionally substituted 5- to 14-membered aromatic heterocyclic group (e.g., thienyl) and (12) an optionally substituted 3- to 14-membered nonaromatic heterocyclic group (e.g., azetidinyl);

$R^1$ is a hydrogen atom, an optionally substituted $C_{1-6}$ alkyl group (e.g., methyl, ethyl, isopropyl) or an optionally substituted $C_{3-10}$ cycloalkyl group;

$R^2$ and $R^3$ are each independently a hydrogen atom, or an optionally substituted $C_{1-6}$ alkyl group (e.g., methyl);

$X^a$ is $CR^a$;

$X^c$ is $CR^c$;

$R^a$ is a hydrogen atom, a halogen atom (e.g., fluorine atom, chlorine atom), an optionally substituted $C_{1-6}$ alkyl group (e.g., methyl, ethyl) or an optionally substituted $C_{1-6}$ alkoxy group (e.g., methoxy);

$R^d$ is a hydrogen atom; and $R^e$ is a hydrogen atom or an optionally substituted $C_{1-6}$ alkyl group (e.g., methyl).

[Compound G]

Compound (I) wherein ring A is a benzene ring optionally further substituted by 1-5 (preferably 1-3, more preferably 1 or 2) substituents selected from (1) a halogen atom (e.g., fluorine atom, bromine atom, iodine atom), (2) a cyano group, (3) a $C_{1-6}$ alkyl group (e.g., methyl, ethyl, propyl, isopropyl, tert-butyl) optionally substituted by 1 to 3 halogen atoms (e.g., fluorine atom), (4) a $C_{1-6}$ alkoxy group (e.g., methoxy, ethoxy) optionally substituted by 1 to 3 halogen atoms (e.g., fluorine atom), (5) a $C_{3-10}$ cycloalkyl group (e.g., cyclopropyl), (6) a carbamoyl group optionally mono- or di-substituted by a $C_{1-6}$ alkyl group (e.g., methyl), (7) a sulfanyl group optionally substituted by 1-6 halogen atoms (e.g., fluorine atom), (8) a $C_{6-14}$ aryloxy group (e.g., phenoxy), (9) a 3- to 14-membered non-aromatic heterocyclyloxy group (e.g., oxetanyloxy), (10) a $C_{3-10}$ cycloalkyloxy group (e.g., cyclobutyloxy), (11) a 5- to 14-membered aromatic heterocyclic group (e.g., thienyl) and (12) a 3- to 14-membered nonaromatic heterocyclic group (e.g., azetidinyl) optionally substituted by 1 to 3 halogen atoms (e.g., fluorine atom);

$R^1$ is (i) a hydrogen atom, or (ii) a $C_{1-6}$ alkyl group (e.g., methyl, ethyl, isopropyl) optionally substituted by 1 to 3 substituents selected from a cyano group, a hydroxy group and a $C_{6-14}$ aryl group (e.g., phenyl);

$R^2$ and $R^3$ are each independently a hydrogen atom or a $C_{1-6}$ alkyl group (e.g., methyl);

$X^a$ is $CR^a$;

$X^c$ is $CR^c$;

$R^a$ is a hydrogen atom, a halogen atom (e.g., fluorine atom, chlorine atom), a $C_{1-6}$ alkyl group (e.g., methyl, ethyl) or a $C_{1-6}$ alkoxy group (e.g., methoxy);

$R^d$ is a hydrogen atom; and $R^e$ is a hydrogen atom or a $C_{1-6}$ alkyl group (e.g., methyl).

[Compound H]

Compound (I) wherein ring A is a benzene ring optionally further substituted by 1-5 (preferably 1-3, more preferably 1 or 2) substituents selected from (1) a $C_{1-6}$ alkoxy group (e.g., methoxy, ethoxy) optionally substituted by 1 to 3 halogen atoms (e.g., fluorine atom), (2) a $C_{1-6}$ alkyl group (e.g., methyl, ethyl, propyl) optionally substituted by 1 to 3 halogen atoms (e.g., fluorine atom), (3) a halogen atom (e.g., fluorine atom, chlorine atom, bromine atom, iodine atom) and (4) a $C_{3-10}$ cycloalkyl group (e.g., cyclopropyl);

$R^1$, $R^2$ and $R^3$ are each a hydrogen atom;

$X^a$ is $CR^a$;

$X^b$ is $CR^b$;

$X^c$ is $CR^c$;

$X^d$ is $CR^d$;

$X^e$ is $CR^e$;

$R^a$ is a hydrogen atom, a $C_{1-6}$ alkyl group (e.g., methyl, ethyl) or a $C_{1-6}$ alkoxy group (e.g., methoxy); and $R^b$, $R^c$, $R^d$ and $R^e$ are each a hydrogen atom.

Specific examples of compound (I) include the below-mentioned compounds of Examples 1-99, preferably 2-(imidazo[1,2-a]pyridin-5-yl)-N-(4-(trifluoromethyl)phenyl)acetamide (Example 1);

2-(imidazo[1,2-a]pyridin-5-yl)-N-(4-methoxyphenyl)acetamide (Example 2); and

N-(3-fluoro-4-methoxyphenyl)-2-(imidazo[1,2-a]pyridin-5-yl)acetamide (Example 8).

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like, alkaline earth metal salts such as calcium salt, magnesium salt and the like, aluminum salt, and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

Compound (I) may be used as a prodrug.

The prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, or t-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like). Any of these compounds can be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, a prodrug may form a salt, and as such salt, those exemplified as a salt of the compound represented by the aforementioned formula (I) can be mentioned.

Compound (I) may be labeled with an isotope (e.g., $^3$H, $^{13}$C, $^{14}$C, $^{18}$F, $^{35}$S, $^{125}$I) and the like.

Compound (I) labeled with or substituted by an isotope can be used, for example, as a tracer used for Positron Emission Tomography (PET) (PET tracer), and is useful in the field of medical diagnosis and the like.

Furthermore, compound (I) may be a hydrate or a non-hydrate, or a non-solvate, or a solvate.

Compound (I) also encompasses a deuterium conversion form wherein $^1$H is converted to $^2$H(D).

Furthermore, compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, and stability). The cocrystal and cocrystal salt can be produced by cocrystallization method known per se.

Compound (I) or a prodrug thereof (hereinafter sometimes to be simply abbreviated as the compound of the present invention) is low in its toxicity and can be used as it is or in the form of a pharmaceutical composition (hereinafter sometimes to be abbreviated as the "medicament of the present invention") by mixing with a pharmacologically acceptable carrier etc. to mammals (e.g., human, mouse, rat, rabbit, dog, cat, bovine, horse, swine, monkey) as an agent for the prophylaxis or treatment of various diseases mentioned below.

As pharmacologically acceptable carriers, various organic or inorganic carrier substances conventionally used as preparation materials can be used. These are incorporated as excipient, lubricant, binder and disintegrant for solid preparations; or solvent, solubilizing agent, suspending agent, isotonicity agent, buffer and soothing agent for liquid preparations; and the like. Where necessary, preparation additives such as preservative, antioxidant, colorant, sweetening agent and the like can also be used.

Preferable examples of the excipient include lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthetic aluminum silicate and magnesium aluminometasilicate.

Preferable examples of the lubricant include magnesium stearate, calcium stearate, talc and colloidal silica.

Preferable examples of the binder include gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone.

Preferable examples of the disintegrant include lactose, sucrose, starch, carboxymethylcellulose, calcium carboxymethylcellulose, croscarmellose sodium, sodium carboxymethyl starch, light anhydrous silicic acid and low-substituted hydroxypropylcellulose.

Preferable examples of the solvent include water for injection, physiological brine, Ringer's solution, alcohol, propylene glycol, polyethylene glycol, sesame oil, corn oil, olive oil and cottonseed oil.

Preferable examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; hydrophilic polymers such as poly(vinyl alcohol), polyvinylpyrrolidone, carboxymethylcellulose sodium, methylcellulose, hydroxymethylcellulose, hydroxyethylcellulose, hydroxypropylcellulose and the like, polysorbates; and polyoxyethylene hydrogenated castor oil.

Preferable examples of the isotonicity agent include sodium chloride, glycerol, D-mannitol, D-sorbitol and glucose.

Preferable examples of the buffer include buffers of phosphate, acetate, carbonate, citrate etc.

Preferable examples of the soothing agent include benzyl alcohol.

Preferable examples of the preservative include p-oxybenzoate esters, chlorobutanol, benzyl alcohol, phenethyl alcohol, dehydroacetic acid and sorbic acid.

Preferable examples of the antioxidant include sulfite salts and ascorbate salts.

Preferable examples of the colorant include aqueous food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the aforementioned aqueous food tar color), natural dyes (e.g., β-carotene, chlorophyll, red iron oxide) and the like.

Preferable examples of the sweetening agent include saccharin sodium, dipotassium glycyrrhizinate, aspartame and stevia.

Examples of the dosage form of the medicament of the present invention include tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop, can be mentioned, which can be administered orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

These preparations may be a release control preparation (e.g., sustained-release microcapsule) such as an immediate-release preparation, a sustained-release preparation and the like.

The medicament of the present invention can be produced according to a method conventionally used in the field of pharmaceutical formulation, for example, the method described in the Japanese Pharmacopoeia, and the like.

While the content of the compound of the present invention in the medicament of the present invention varies depending on the dosage form, dose of the compound of the present invention and the like, it is, for example, about 0.1 to 100 wt %.

When an oral preparation is produced, coating may be applied where necessary for the purpose of taste masking, enteric solubility or sustainability.

Examples of the coating base used for coating include sugar coating base, water-soluble film coating base, enteric film coating base, and sustained-release film coating base.

As the sugar coating base, sucrose is used, and one or more kinds selected from talc, precipitated calcium carbonate, gelatin, gum arabic, pullulan, and carnauba wax may be further used in combination.

Examples of the water-soluble film coating base include cellulose polymers such as hydroxypropylcellulose, hydroxypropylmethylcellulose, hydroxyethylcellulose, methylhydroxyethylcellulose and the like; synthetic polymers such as polyvinyl acetal diethylaminoacetate, aminoalkylmethacrylate copolymer E [Eudragit E (trade name)], polyvinylpyrrolidone and the like; and polysaccharides such as pullulan and the like.

Examples of the enteric film coating base include cellulose polymers such as hydroxypropylmethylcellulose phthalate, hydroxypropylmethylcellulose acetate succinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; and naturally-occurring substances such as shellac and the like.

Examples of the sustained-release film coating base include cellulose polymers such as ethylcellulose and the like; and acrylic acid polymers such as aminoalkylmethacrylate copolymer RS [Eudragit RS (trade name)], ethyl acrylate-methyl methacrylate copolymer suspension [Eudragit NE (trade name)] and the like.

Two or more kinds of the above-mentioned coating bases may be used in a mixture at an appropriate ratio. In addition, for example, light shielding agents such as titanium oxide, and red ferric oxide may also be used during coating.

Since the compound of the present invention shows low toxicity (e.g., acute toxicity, chronic toxicity, genetic toxicity, reproductive toxicity, pulmonary toxicity, carcinogenicity) and less side effects, it can be used as a prophylactic or therapeutic agent, or diagnostic agent for various diseases in mammals.

The compound of the present invention can be used as a prophylactic or therapeutic agent for central and peripheral diseases. For example, it is expected to be useful as an agent for the prophylaxis or treatment of diseases such as (1) psychiatric diseases [e.g., depression, major depression, minor depressive disorder, bipolar depression, dysthymic disorder, emotional disorder (seasonal affective disorder and the like), recurrent depression, postpartum depression, stress disorder, major depressive disorder concomitant with psychosis (including delusive disorders and schizophrenia), manic or mixed mood episode, hypomanic mood episode, depression episode with atypical features, depression episode with melancholic features, depressive episodes with tonic features, depression episode after stroke, delirium, peripheral symptoms of dementia (mental symptoms or behavior abnormalities), anxiety, generalized anxiety disorder, anxiety syndrome, mood disorder, cyclothymic disorder, premenstrual dysphoric disorder, panic disorder, phobia, social phobia, social anxiety disorder, obsessive disorder, post-traumatic stress syndrome, post-traumatic stress disorder, delusions or depression-type schizoaffective disorder, delusive personality disorder, Tourette syndrome, autism, fragile X syndrome, Rett syndrome, adjustment disorder, bipolar disorder (including type I bipolar disorder and type II bipolar disorder), neurosis, schizophrenia (e.g., positive symptom, negative symptom, memory disorders, delusional schizophrenia, disorganized schizophrenia, tension type schizophrenia, undifferentiated schizophrenia, remnant type schizophrenia), schizophreniform disorder, chronic fatigue syndrome, anxiety neurosis, compulsive neurosis, panic disorder, epilepsy, anxiety, anxious mental state, emotional abnormality, cyclothymia, nervous erethism, faint, addiction, low sex drive, attention deficit hyperactivity disorder (ADHD), refractory major depression, treatment-resistant depression, psychotic disturbance (e.g., short-term psychotic disorder, shared psychotic disorder), psychosis induced by alcohol, amphetamine, cannabis, cocaine, hallucinogen, obesity, inhalation medicine, opioids or phencyclidine, delusional disorder, Noonan syndrome, Angelman syndrome, Prader-Willi syndrome, Beckwith-Wiedemann syndrome, Silver-Russell syndrome, tuberous sclerosis, Williams syndrome, Kallmann syndrome, Rubinstein-Taybi syndrome], movement disorder, mental retardation, paranoid tendency, (2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, alcoholic dementia or other drug related dementia, dementia associated with intracranial tumor or brain trauma, Dementia associated with Huntington's disease or Parkinson's disease, neurodegeneration accompanying brain trauma, neurodegeneration accompanying stroke, neurodegeneration accompanying cerebral infarction, neurodegeneration associated with hypoglycemia, neurodegeneration accompanying epileptic seizures, neurodegeneration accompanying neurotoxicosis, multiple system atrophy, spinal cord injury, Aids-related dementia, progressive supranuclear palsy, Pick's syndrome, Niemann-Pick syndrome, corticobasal degeneration, Down's syndrome, vascular dementia, post-encephalitic parkinsonism, dementia with Lewy bodies, HIV dementia, amyotrophic lateral sclerosis (ALS), motor neurogenesis disease (MND), Creutzfeldt-Jakob disease or prion disease, cerebral palsy, progressive supranuclear palsy, multiple sclerosis, neuromyopathy], (3) amnestic disorder, mild cognitive impairment, learning disability (e.g., reading disturbance, arithmetic disorder, dysgraphia), age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) pain [e.g., psychogenic pain (somatoform disorder, pain disorder, somatization disorder, hypochondriasis, conversion disorder, chronic pain accompanied by depression), inflammatory pain, peripheral neuropathic pain, central neuropathic pain, neuropathic pain, acute pain, intractable pain, cancerous continuous pain, cancerous breakthrough pain, cancer pain, continuous pain, physical pain, breakthrough pain, chronic pain, tenderness, generalized pain, dull pain, dermatological pain, radiation pain, pain, postoperative thoracotomy pain syndrome], (7) deafness [e.g., kanamycin deafness, streptomycin deafness, toxic deafness, senile deafness, idiopathic bilateral sensorineural hearing loss, sudden deafness, acquired deaf mutism, genetic deafness, organic deafness, high-tone sensorineural hearing loss, occupational hearing loss, occupational hearing loss, low-tone sensorineural hearing loss], (8) traumatic brain injury, and disorder or complication associated therewith, post concussive syndrome, shaken baby syndrome, cerebral apoplexy, age-related macular degeneration, oculopalatal tremor, convulsions, phantom limb pain, radiation somnolence syndrome, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug abuse, drug dependence, drug withdrawal, migraine, stress headache, catatonic headache, diabetic neuropathy, obesity, diabetes, muscular convulsions, Meniere's disease, autonomic ataxia, alopecia, glaucoma, hypertension, cardiac disease, tachycardia, congestive cardiac failure, breathing, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, diarrhea, constipation, postoperative ileus, and the like.

Particularly, the compound of the present invention is useful for the prophylaxis or treatment of major depression, bipolar disorder, migraine, pain or peripheral symptoms of dementia.

Both major depression and bipolar disorder are classified as mood disorder, and are diseases showing depression state or depression state and manic state for a long term. In recent years, it has been found that continuous intravenous administration of ketamine, an NMDA receptor antagonist, improves depression symptom accompanying major depression and bipolar disorder rapidly and in a sustained manner (Therapeutic Advances in Psychopharmacology, vol. 4, pp. 75-99, 2014). It has also been reported that continuous intravenous administration of CP-101, 606, which are antagonists of NMDA receptor containing the NR2B subunit significantly improves treatment resistant-depression symptom (Journal of Clinical Psychopharmacology, vol. 28, pp. 631-637, 2008). Therefore, an antagonist of an NMDA receptor containing the NR2B subunit, which is the target of the present invention, is promising as a prophylactic or therapeutic drug for treatment resistant-depression disease.

Migraine is a chronic and paroxysmal primary headache. While the onset mechanism is unknown, it is considered to be developed along with abnormalities of central nervous system process, abnormalities of trigeminal nerve blood vessel system and the like. In pathophysiology study of migraine, particularly aura thereof, a cortical spreading depression phenomenon is attracting attention. It has been reported that CP-101, 606 and Ro25-6981, which are antagonists of NMDA receptor containing the NR2B subunit, suppress the number of occurrence and the depth of cortical spreading depression in an experimental cortical spreading depression test using rodents (the Journal of Pharmacology and Experimental Therapeutics, vol. 321, pp. 564-572, 2007). Therefore, an antagonist of an NMDA receptor containing the NR2B subunit, which is the target of the present invention, is promising as a prophylactic or therapeutic drug for migraine.

Pain is classified into acute pain whose pain lasts for a comparatively short period of time, and chronic pain accompanying retention or recurrence for 3 months or longer, retention for not less than one month after recovery of acute tissue injury, or an unhealed lesion. An NMDA receptor containing the NR2B subunit is highly expressed in posterior horn of spinal cord which plays an important role in the acceptance of pain, and functional control thereof is suggested to enable pain control. In fact, a genetic modification operation that causes functional decline of NR2B subunit has been reported to elevate the pain sense threshold (European Journal of Neuroscience, vol. 32, pp. 798-810, 2010). Also, it has been reported that the pain sense threshold increases due to Ifenprodil as an antagonist of an NMDA receptor containing the NR2B subunit (Pain, vol. 153, pp. 1022-1029, 2012). Therefore, an antagonist of an NMDA receptor containing the NR2B subunit, which is the target of the present invention, is promising as a prophylactic or therapeutic drug for pain.

Dementia refers to chronic, general, and generally irreversible decline of cognition. While the degradation of quality of life of patients due to the cognitive decline is remarkable, peripheral symptoms of dementia (psychological symptom or abnormal behavior) is also considered to be a factor markedly influencing the quality of life of patients and caregiver thereof. An effective therapeutic intervention method for peripheral symptoms of dementia has not been established; however, it has been reported that administration of memantine, which is an NMDA receptor antagonist, partially improves peripheral symptoms of dementia (Annals of Pharmacotherapy, vol. 42, pp. 32-38, 2007). While NMDA receptor containing the NR2B subunit is widely distributed in the brain except cerebellum, peripheral symptoms of dementia has been reported to be related to white matter abnormality of brain region except cerebellum (Journal of the Neurological Sciences, vol. 337, pp. 162-166, 2014). Therefore, an antagonist of an NMDA receptor containing the NR2B subunit, which is the target of the present invention, is promising as a prophylactic or therapeutic drug for peripheral symptoms of dementia.

While the dose of the compound of the present invention varies depending on the subject of administration, administration route, target disease, symptom and the like, for example, when the compound of the present invention is administered orally to an adult patient, its dose is for example, about 0.01 to 100 mg/kg body weight per dose, preferably 0.1 to 50 mg/kg body weight per dose and more preferably 0.5 to 20 mg/kg body weight per dose. This amount is desirably administered in one to 3 portions daily.

The compound of the present invention can be used in combination with other active ingredients (hereinafter to be abbreviated as concomitant drug).

Examples of the concomitant drug include, but are not limited to, the following. Acetylcholine esterase inhibitor (e.g., donepezil, rivastigmine, galanthamine, zanapezil), antidementia agent (e.g., memantine), inhibitor of β amyloid protein production, secretion, accumulation, aggregation and/or deposition, β secretase inhibitor (e.g., 6-(4-biphenylyl)methoxy-2-[2-(N,N-dimethylamino)ethyl]tetralin, 6-(4-biphenylyl)methoxy-2-(N,N-dimethylamino)methyltetralin, 6-(4-biphenylyl)methoxy-2-(N,N-dipropylamino)methyltetralin, 2-(N,N-dimethylamino)methyl-6-(4'-methoxybiphenyl-4-yl)methoxytetralin, 6-(4-biphenylyl)methoxy-2-[2-(N,N-diethylamino)ethyl]tetralin, 2-[2-(N,N-dimethylamino)ethyl]-6-(4'-methylbiphenyl-4-yl)methoxytetralin, 2-[2-(N,N-dimethylamino)ethyl]-6-(4'-methoxybiphenyl-4-yl)methoxytetralin, 6-(2',4'-dimethoxybiphenyl-4-yl)methoxy-2-[2-(N,N-dimethylamino)ethyl]tetralin, 6-[4-(1,3-benzodioxol-5-yl)phenyl]methoxy-2-[2-(N,N-dimethylamino)ethyl]tetralin, 6-(3',4'-dimethoxybiphenyl-4-yl)methoxy-2-[2-(N,N-dimethylamino)ethyl]tetralin, an optically active form thereof, a salt thereof and a hydrate thereof, OM99-2 (WO001/00663)), γ secretase inhibitor, β amyloid protein aggregation inhibitor (e.g., PTI-00703, ALZHEMED (NC-531), PPI-368 (National Publication of International Patent Application No. 11-514333), PPI-558 (National Publication of International Patent Application No. 2001-500852), SKF-74652 (Biochem. J. (1999), 340(1), 283-289)), β amyloid vaccine, β amyloid-degrading enzyme and the like, brain function enhancer (e.g., aniracetam, nicergoline), other therapeutic drug for Parkinson's disease [(e.g., dopamine receptor agonist (e.g., L-DOPA, bromocriptine, pergolide, talipexole, pramipexole, cabergoline, amantadine), monoamine oxidase enzyme (MAO) inhibitor (e.g., deprenyl, selegiline, remacemide, riluzole), anticholinergic agent (e.g., trihexyphenidyl, biperiden), COMT inhibitor (e.g., entacapone)], therapeutic drug for amyotrophic lateral sclerosis (e.g., riluzole etc., neurotrophic factor), therapeutic drug for abnormal behavior accompanying progress of dementia, wandering and the like (e.g., sedative, anti-anxiety drug), apoptosis inhibitor (e.g., CPI-1189, IDN-6556, CEP-1347), neuronal differentiation/regeneration promoter (e.g., leteprinim, xaliproden; SR-57746-A), SB-216763, Y-128, VX-853, prosaptide, 5,6-dimethoxy-2-[2,2,4,6,7-pentamethyl-3-(4-methylphenyl)-2,3-dihydro-1-benzofuran-5-yl]isoindoline, 5,6-dimethoxy-2-[3-(4-isopropylphenyl)-2,2,4,6,7-pentamethyl-2,3-dihydro-1-benzofuran-5-yl]isoindoline, 6-[3-(4-isopropylphenyl)-2,2,4,6,7-pentamethyl-2,3-dihydro-1-benzofuran-5-yl]-6,7-dihydro-5H-[1,3]dioxolo[4,5-f]isoindole and an optically active form, salt or hydrate thereof), non-steroidal antiinflammatory agents (meloxicam, tenoxicam, indomethacin, ibuprofen, celecoxib, rofecoxib, aspirin, indomethacin etc.), steroid drug (dexamethasone, hexestrol, cortisone acetate etc.), disease-modifying anti-rheumatic drug (DMARDs), anti-cytokine drug (e.g., TNF inhibitor, MAP kinase inhibitor), therapeutic agent for incontinence, frequent urination (e.g., flavoxate hydrochloride, oxybutynin hydrochloride, propiverine hydrochloride), phosphodiesterase inhibitor (e.g., sildenafil(citrate)), dopamine agonist (e.g., apomorphine), antiarrhythmic drugs (e.g., mexiletine), sex hormone or a derivative thereof (e.g., progesterone, estradiol, estradiol benzoate), therapeutic agent for osteoporosis (e.g., alfacalcidol, calcitriol, elcatonin, calcitonin salmon, estriol, ipriflavone, pamidronate disodium, alendronate sodium hydrate, incadronate disodium), parathyroid hormone (PTH), calcium receptor antagonists, therapeutic drug for insomnia (e.g., benzodiazepines medicament, non-benzodiazepines medicament, melatonin agonist, orexin receptor antagonists), therapeutic drug for schizophrenia (e.g., typical antipsychotic agents such as haloperidol and the like; atypical antipsychotic agents such as clozapine, olanzapine, risperidone, aripiprazole and the like; medicament acting on metabotropic glutamate receptor or ion channel conjugated-type glutamate receptor; phosphodiesterase inhibitor), benzodiazepines medicament (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), mirtazapine, trazodone hydrochloride, nefazodone hydrochloride, bupropion hydrochloride, setiptiline maleate, 5-HT$_{1A}$ agonist, (buspirone hydrochloride, tandospirone citrate, osemozotan hydrochloride etc.), 5-HT$_{2A}$ antagonist, 5-HT$_{2A}$ inverse agonist, 5-HT$_3$ antagonist (cyamemazine etc.), heart non-selective p inhibitor (propranolol hydrochloride, oxprenolol hydrochloride etc.), histamine H$_1$ antagonist (hydroxyzine hydrochloride etc.), CRF antagonist, other antianxiety drug (meprobamate etc.), tachykinin antagonist (MK-869, saredutant etc.), medicament that acts on metabotropic glutamate receptor, CCK antagonist, β adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin Via antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for ALS (riluzole etc., neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), antiobesity drug, therapeutic drug for diabetes, therapeutic agent for diabetic complications, therapeutic drug for hypertension, therapeutic drug for hypotension, diuretic, chemotherapeutic agent, immunotherapeutic agent, antithrombotic agent, anti-cancer agent, antibody medicament, nucleic acid or nucleic acid derivative, aptamer drug and the like.

Two or more kinds of the above-mentioned concomitant drugs may be used in combination at an appropriate ratio.

When the compound of the present invention is applied to each of the above-mentioned diseases, it can also be used in combination with biologics (e.g., antibody, vaccine preparation), or can be combined with a gene therapy method and the like and applied as a combination therapy, or can also be used in combination with a treatment in psychiatric field without using drugs.

Examples of the antibody and vaccine preparation include vaccine preparation against angiotensin II, vaccine preparation against CETP, CETP antibody, antibody against TNFα antibody and other cytokines, amyloid P vaccine preparation, vaccine for type 1 diabetes (e.g., DIAPEP-277 of Peptor), anti-HIV antibody and HIV vaccine preparation, as well as antibodies or vaccine preparations against cytokines, renin-angiotensin type enzymes and products thereof, antibodies or vaccine preparations against enzymes or proteins involved in blood lipid metabolism, antibodies or vaccines relating to enzymes and proteins involved in blood coagulation or fibrinolysis system, antibodies or vaccine preparations against proteins involved in sugar metabolism and insulin resistance, and the like. In addition, it can be used in combination with biologics relating to growth factors such as GH, IGF and the like.

Examples of the gene therapy method include a treatment method using gene relating to cytokine, renin-angiotensin type enzyme and product thereof, G protein, G protein conjugated receptor and phosphorylating enzyme thereof, a treatment method using a DNA decoy such as NFκB decoy and the like, a treatment method using antisense, a treatment method using a gene relating to a enzyme or protein involved in blood lipid metabolism (e.g., a gene relating to metabolism, excretion and absorption of cholesterol or triglyceride or HDL-cholesterol or blood phospholipid), a treatment method using a gene relating to a enzyme or protein involved in angiogenesis therapy for peripheral vascular obstruction and the like (e.g., growth factors such as HGF, VEGF etc.), a treatment method using a gene relating to a protein involved in glucose metabolism and insulin resistance, antisense against cytokines such as TNF etc., and the like.

Examples of the treatment method in the psychiatric field without using drug include modified electroconvulsive therapy, deep brain stimulation therapy, repetitive transcranial magnetic stimulation therapy, psychotherapy including cognitive behavioral therapy and the like.

It can also be used in combination with various organ regeneration methods such as cardiac regeneration, renal regeneration, pancreatic regeneration, revascularization and the like, cell transplantation therapy utilizing bone marrow cells (bone marrow-derived mononuclear cell, myelogenic stem cell), or artificial organ utilizing tissue engineering (e.g., artificial blood vessel, cardiomyocyte sheet).

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination agent of the present invention is not particularly restricted, and it is sufficient that the compound of the present invention and the concomitant drug are combined in administration. Examples of the administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The dose of the concomitant drug can be appropriately determined based on the dose employed in clinical situations. The mixing ratio of the compound of the present invention and a concomitant drug can be appropriately determined depending on the administration subject, administration route, target disease, symptom, combination and the like.

For example, the content of the compound of the present invention in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of the concomitant drug in the combination agent of the present invention differs depending on the form of a preparation, and usually from about 0.01 to 100 wt %, preferably from about 0.1 to 50 wt %, further preferably from about 0.5 to 20 wt %, based on the whole preparation.

The content of additives such as a carrier and the like in the combination agent of the present invention differs depending on the form of a preparation, and usually from about 1 to 99.99 wt %, preferably from about 10 to 90 wt %, based on the whole preparation.

When the compound of the present invention and a concomitant drug are separately formulated into preparations, the contents thereof are similar to the above.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably 1 atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature—300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and water.

Two or more kinds of the above-mentioned solvents may be used by mixing at an appropriate ratio.

When a base is used in the reaction of each step, for example, bases shown below or those described in Examples are used.

inorganic bases: sodium hydroxide, magnesium hydroxide and the like;
basic salts: sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyl disilazide and the like; and
organic lithiums: n-butyllithium and the like.

When an acid or acidic catalyst is used in the reaction of each step, for example, acids and acidic catalysts shown below or those described in Examples are used.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like; and
Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, t-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as t-butylcarbonate and the like, and the like.

Examples of the protecting group of the carbonyl group of aldehyde include acetal protecting groups such as dimethyl acetal and the like; cyclic acetal protecting groups such as cyclic 1,3-dioxane and the like, and the like.

Examples of the protecting group of the carbonyl group of ketone include ketal protecting groups such as dimethyl ketal and the like; cyclic ketal protecting groups such as cyclic 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, t-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5,6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include combination of phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include combination of Lewis acid and acid chloride or combination of Lewis acid and alkylating agents (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., basic salts, organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include arylmagnesium halides such as phenylmagnesium bromide and the like; and alkylmagnesium halides such as methylmagnesium bromide and the like. The Grignard reagent can be prepared by a method known Jo per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium borohydride, sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include ammonia, primary amines such as methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and the like. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphate (HATU); sulfuric acid; a combination thereof and the like. When a carbodiimide condensing agent is used, additives such as l-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, basic salts and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl)-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a alkyl halide form from alcohol by reacting with triphenylphosphine and carbon tetrachloride or carbon tetrabromide, and the like may be used. Alternatively, a method of synthesizing a alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include combination of alkyl halides such as ethyl bromoacetate and the like; and phosphites such as triethyl phosphite, tri(isopropyl) phosphite and the like.

When a sulfonate esterification reaction is performed in each step, examples of the sulfonylating agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of t-butyl ester is performed, formic acid, triethylsilane and the like are sometimes added to reductively trap the by-produced t-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

Compound (I) can be produced from intermediate (1) by the following production step A.

[Production Step A]

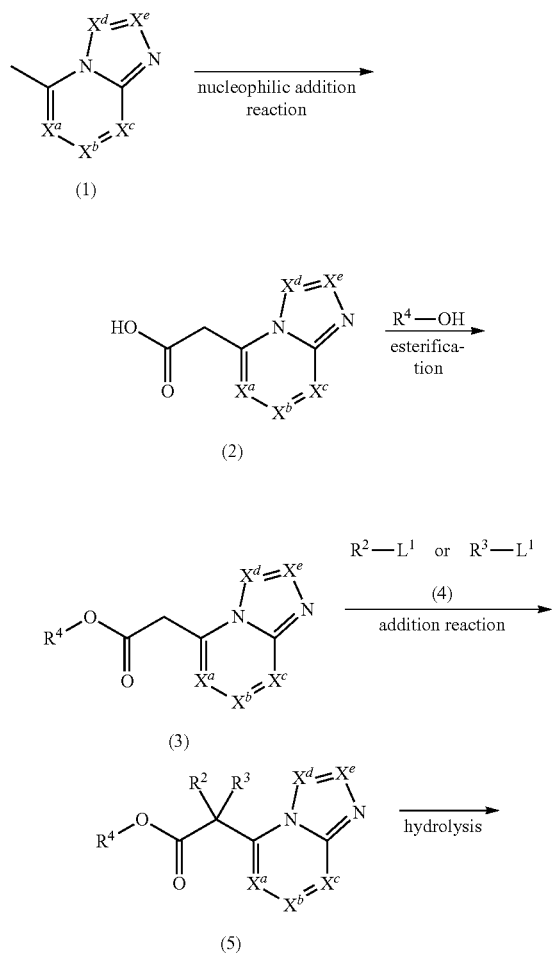

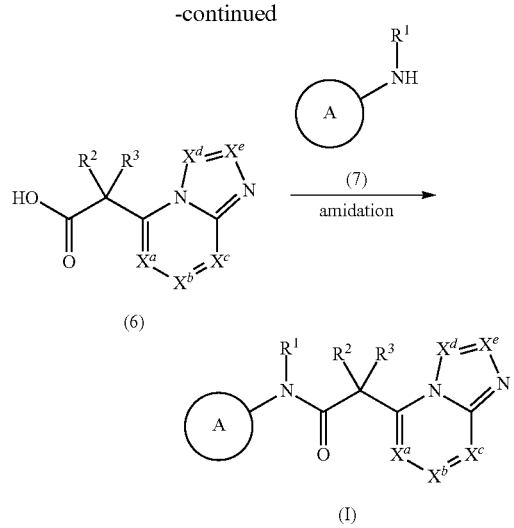

wherein $R^4$ is a lower alkyl group, $L^1$ is a leaving group, and $X^a$-$X^e$, ring A and $R^1$-$R^3$ mean the same as above.

Intermediate (2) can be produced by a nucleophilic addition reaction of intermediate (1). As the base to be used, organic lithiums, metal amides and the like can be mentioned.

Intermediate (3) can be produced by esterification of intermediate (2) by using an alcohol represented by the formula: $R^4$—OH.

Intermediate (5) can be produced by an addition reaction of intermediate (3) by using an alkylating agent (4) represented by the formula: $R^2$-$L^1$ or $R^3$-L. As an alkylating agent, alkyl halide and the like can be mentioned.

Intermediate (6) can be produced by hydrolysis of intermediate (5).

Compound (I) can be produced by amidation of intermediate (6) by using amine compound (7).

Intermediate (3) can also be produced from intermediate (8) by the following Production step B.

[Production Step B]

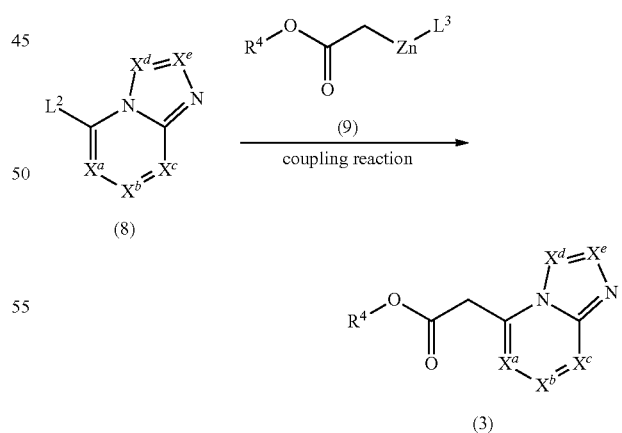

wherein $L^2$ is a leaving group, $L^3$ is a halogen atom, and $R^4$ and $X^a$-$X^e$ mean the same as above.

Intermediate (3) can be produced by a coupling reaction of intermediate (8) and organic zinc compound (9).

In the thus-obtained compound (I), an intramolecular functional group can also be converted to an object functional group by combining chemical reactions known per se. Examples of the chemical reaction include oxidation reaction, reduction reaction, alkylation reaction, acylation reaction, urea formation reaction, hydrolysis reaction, amination reaction, esterification reaction, aryl coupling reaction, deprotection reaction and the like.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is extremely useful as a medicament.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, the indication of NH means use of aminopropylsilane-bonded silica gel, Diol means use of 3-(2,3-dihydroxypropoxy)propylsilane-bonded silica gel and DiNH means use of N-(2-aminoethyl)-3-aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In Examples below, the following abbreviations are used.
MS: mass spectrum
[M+H]$^+$, [M−H]$^-$: molecular ion peak
M: mol concentration
N: normal
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: Electron Spray Ionization
APCI: atmospheric pressure chemical ionization
THF: tetrahydrofuran
DME: 1,2-dimethoxyethane
DMF: N,N-dimethylformamide
DMA: N,N-dimethylacetamide
HATU: 2-(7-azabenzotriazol-1-yl)-1,1,3,3-tetramethyluronium hexafluorophosphate
HOBt: 1-hydroxybenzotriazole
DIPEA: N,N-diisopropylethylamine
IPE: diisopropyl ether $^1$H NMR was measured by Fourier-transform NMR. For the analysis, ACD/SpecManager (trade name) and the like were used. Very mild peaks for protons of a hydroxy group, an amino group and the like are not described.

MS was measured by LC/MS. As ionization, ESI method, or APCI method was used. The data indicates those found. Generally, molecular ion peaks ([M+H]$^+$, [M−H]$^-$ etc.) are observed. When a compound has a tert-butoxycarbonyl group, a peak without a tert-butoxycarbonyl group or a tert-butyl group may be observed as a fragment ion. In addition, when a compound has a hydroxyl group, a peak without H$_2$O may be observed as a fragment ion. In the case of a salt, generally, a molecular ion peak or a fragment ion peak of a free form is observed.

The unit of sample concentration (c) in optical rotation ([α]$_D$) is g/100 mL.

The elemental analytical value (Anal.) shows Calculated value (Calcd) and Found value (Found).

Example 1

2-(imidazo[1,2-a]pyridin-5-yl)-N-(4-(trifluoromethyl)phenyl)acetamide

To a mixture of 2-(imidazo[1,2-a]pyridin-5-yl)acetic acid (1.0 g), 4-(trifluoromethyl)aniline (1.1 g), and anhydrous DMF (19 mL) were added triethylamine (0.95 mL), HOBt monohydrate (1.0 g) and 1-ethyl-3-(3-dimethylaminopropyl)carbodiimide hydrochloride (1.3 g) at room temperature, and the mixture was stirred at room temperature overnight. The reaction mixture was poured into water, and the mixture was extracted with ethyl acetate. The extract was washed with water and saturated brine, and dried over anhydrous magnesium sulfate. The solvent was evaporated under reduced pressure. The obtained residue was purified by silica gel column chromatography (NH, ethyl acetate/methanol), and recrystallized from THF-hexane to give the title compound (0.89 g).

$^1$H NMR (300 MHz, DMSO-d$_6$) δ4.21 (2H, s), 6.90 (1H, d, J=6.8 Hz), 7.26 (1H, dd, J=9.1, 6.8 Hz), 7.55 (1H, d, J=9.1 Hz), 7.62 (1H, d, J=1.3 Hz), 7.66-7.73 (2H, m), 7.75-7.85 (2H, m), 7.86-7.95 (1H, m), 10.77 (1H, s).

Example 2

2-(imidazo[1,2-a]pyridin-5-yl)-N-(4-methoxyphenyl)acetamide (A) 5-methylimidazo[1,2-a]pyridine A mixture of 6-methylpyridin-2-amine (5.0 g), 40% aqueous chloroacetaldehyde solution (9.1 mL), and ethanol (100 mL) was heated under reflux overnight. The reaction mixture was cooled to room temperature and the solvent was evaporated under reduced pressure. The obtained residue was neutralized with saturated aqueous sodium hydrogen carbonate solution, and extracted with ethyl acetate. The extract was dried over anhydrous magnesium sulfate, and the solvent was evaporated under reduced pressure. The obtained residue was purified by NH silica gel column chromatography (hexane/ethyl acetate) to give the title compound (6.2 g).

$^1$H NMR (300 MHz, CDCl$_3$) δ2.60 (3H, s), 6.63 (1H, d, J=6.8 Hz), 7.15 (1H, dd, J=9.0, 6.8 Hz), 7.49 (1H, s), 7.55 (1H, d, J=9.0 Hz), 7.70 (1H, d, J=1.1 Hz).

(B) 2-(imidazo[1,2-a]pyridin-5-yl)acetic acid hydrochloride

To a solution of diisopropylamine (7.9 mL) in THF (50 mL) was added 1.6 M n-butyllithium hexane solution (32 mL) at −78° C. The mixture was stirred at the same temperature for 30 min, and a solution of 5-methylimidazo[1,2-a]pyridine (6.2 g) in THF (50 mL) was added dropwise to the reaction mixture. Under an argon gas atmosphere, the reaction product was stirred at −78° C. for 1 hr, dry ice was added and the reaction mixture was heated to room temperature. The solvent was evaporated under reduced pressure, and the residue was diluted with 2 M aqueous sodium hydroxide solution. The aqueous layer was washed 3 times with ethyl acetate, acidified with 2 M hydrochloric acid, and concentrated under reduced pressure. The residue was treated with methanol, insoluble material was filtered off, and the filtrate was concentrated under reduced pressure. The obtained solid was washed with ethyl acetate to give the title compound (4.2 g).

$^1$H NMR (300 MHz, DMSO-d$_6$) δ4.31-4.43 (2H, m), 7.44-7.55 (1H, m), 7.91-7.99 (2H, m), 8.27 (1H, d, J=2.3 Hz), 8.41 (1H, d, J=2.3 Hz), 13.17 (1H, brs).

(C) 2-(imidazo[1,2-a]pyridin-5-yl)-N-(4-methoxyphenyl)acetamide

To a mixture of 2-(imidazo[1,2-a]pyridin-5-yl)acetic acid hydrochloride (400 mg), p-anisidine (230 mg), and anhydrous DMF (2.0 mL) were added triethylamine (0.79 mL), HOBt monohydrate (290 mg) and 1-ethyl-3-(3-dimethylaminopropyl)carbodiimide hydrochloride (540 mg) at room temperature, and the mixture was stirred at room temperature overnight. The obtained residue was purified by silica gel column chromatography (NH, ethyl acetate/methanol). A similar reaction was performed with one more batch, the two resultant products were combined, purified again by silica gel column chromatography (NH, ethyl acetate/methanol) and recrystallized from ethyl acetate to give the title compound (410 mg).

$^1$H NMR (300 MHz, DMSO-d$_6$) δ3.72 (3H, s), 4.10 (2H, s), 6.82-6.92 (3H, m), 7.25 (1H, dd, J=9.1, 6.8 Hz), 7.45-7.57 (3H, m), 7.62 (1H, d, J=1.3 Hz), 7.81-7.91 (1H, m), 10.28 (1H, s).

Example 3

N-(4-ethylphenyl)-2-(imidazo[1,2-a]pyridin-5-yl)acetamide

To a mixture of 2-(imidazo[1,2-a]pyridin-5-yl)acetic acid (50 mg) and anhydrous DMF (1.9 mL) were added 4-ethylaniline (0.042 mL), HATU (160 mg) and DIPEA (0.059 mL) at room temperature, and the mixture was stirred at room temperature for 22 hr. To the reaction mixture were added water, saturated brine and saturated aqueous sodium hydrogen carbonate solution, and the mixture was extracted with ethyl acetate. The obtained organic layer was dried over anhydrous magnesium sulfate and the solvent was evaporated under reduced pressure. The obtained residue was purified by silica gel column chromatography (NH, ethyl acetate/methanol), and recrystallized from ethyl acetate-hexane to give the title compound (36 mg).

$^1$H NMR (300 MHz, DMSO-d$_6$) δ1.15 (3H, t, J=7.5 Hz), 2.46-2.61 (2H, m), 4.12 (2H, s), 6.88 (1H, d, J=6.8 Hz), 7.15 (2H, d, J=8.3 Hz), 7.25 (1H, dd, J=9.0, 6.8 Hz), 7.45-7.57 (3H, m), 7.61 (1H, d, J=1.1 Hz), 7.87 (1H, s), 10.33 (1H, s).

Example 4

N-(4-cyclopropylphenyl)-2-(imidazo[1,2-a]pyridin-5-yl)acetamide

To a mixture of 2-(imidazo[1,2-a]pyridin-5-yl)acetic acid (50 mg) and anhydrous DMF (1.9 mL) were added 4-cyclopropylaniline (45 mg), HATU (160 mg) and DIPEA (0.059 mL) at room temperature, and the mixture was stirred at room temperature for 22 hr. To the reaction mixture were added water, saturated brine and saturated aqueous sodium hydrogen carbonate solution, and the mixture was extracted with ethyl acetate. The obtained organic layer was dried over anhydrous magnesium sulfate and the solvent was evaporated under reduced pressure. The obtained residue was purified by silica gel column chromatography (NH, ethyl acetate/methanol) and recrystallized from ethyl acetate-hexane to give the title compound (22 mg).

$^1$H NMR (300 MHz, DMSO-d$_6$) δ0.55-0.65 (2H, m), 0.84-0.95 (2H, m), 1.77-1.92 (1H, m), 4.11 (2H, s), 6.88 (1H, d, J=6.9 Hz), 7.02 (2H, d, J=8.7 Hz), 7.25 (1H, dd, J=9.0, 6.8 Hz), 7.46 (2H, d, J=8.7 Hz), 7.53 (1H, d, J=9.0 Hz), 7.61 (1H, d, J=1.1 Hz), 7.86 (1H, s), 10.32 (1H, s).

Example 5

2-(imidazo[1,2-a]pyridin-5-yl)-N-(4-(trifluoromethoxy)phenyl)acetamide

To a mixture of 2-(imidazo[1,2-a]pyridin-5-yl)acetic acid (50 mg) and anhydrous DMF (1.9 mL) were added 4-(trifluoromethoxy)aniline (0.046 mL), HATU (160 mg) and DIPEA (0.059 mL) at room temperature, and the mixture was stirred at room temperature for 18 hr. To the reaction mixture were added water, saturated brine and saturated aqueous sodium hydrogen carbonate solution, and the mixture was extracted with ethyl acetate. The obtained organic layer was dried over anhydrous magnesium sulfate and the solvent was evaporated under reduced pressure. The obtained residue was purified by silica gel column chromatography (NH, ethyl acetate/methanol) and recrystallized from ethyl acetate-hexane to give the title compound (40 mg).

$^1$H NMR (300 MHz, DMSO-d$_6$) δ 4.17 (2H, s), 6.90 (1H, d, J=6.8 Hz), 7.26 (1H, dd, J=9.0, 7.2 Hz), 7.33 (2H, d, J=8.7 Hz), 7.54 (1H, d, J=9.0 Hz), 7.62 (1H, d, J=1.1 Hz), 7.70 (2H, d, J=9.0 Hz), 7.87 (1H, s), 10.62 (1H, s).

Example 6

N-(4-(difluoromethoxy)phenyl)-2-(imidazo[1,2-a]pyridin-5-yl)acetamide

To a mixture of 2-(imidazo[1,2-a]pyridin-5-yl)acetic acid (50 mg) and anhydrous DMF (1.9 mL) were added 4-(difluoromethoxy)aniline (54 mg), HATU (160 mg) and DIPEA (0.059 mL) at room temperature, and the mixture was stirred at room temperature for 17 hr. To the reaction mixture were added water, saturated brine and saturated aqueous sodium hydrogen carbonate solution, and the mixture was extracted with ethyl acetate. The obtained organic layer was dried over anhydrous magnesium sulfate and the solvent was evaporated under reduced pressure. The obtained residue was purified by NH silica gel column chromatography (NH, ethyl acetate/methanol) and recrystallized from ethanol-hexane to give the title compound (31 mg).

$^1$H NMR (300 MHz, DMSO-$d_6$) δ4.14 (2H, s), 6.84-7.41 (5H, m), 7.54 (1H, d, J=9.0 Hz), 7.58-7.66 (3H, m), 7.87 (1H, s), 10.50 (1H, s).

Example 7

N-(4-chloro-3-fluorophenyl)-2-(imidazo[1,2-a]pyridin-5-yl)acetamide

To a mixture of 2-(imidazo[1,2-a]pyridin-5-yl)acetic acid (50 mg) and anhydrous DMF (1.9 mL) were added 4-chloro-3-fluoroaniline (50 mg), HATU (160 mg) and DIPEA (0.059 mL) at room temperature, and the mixture was stirred at room temperature for 17 hr. To the reaction mixture were added water, saturated brine and saturated aqueous sodium hydrogen carbonate solution, and the mixture was extracted with ethyl acetate. The obtained organic layer was dried over anhydrous magnesium sulfate and the solvent was evaporated under reduced pressure. The obtained residue was purified by silica gel column chromatography (NH, hexane/ethyl acetate and ethyl acetate/methanol) and recrystallized from ethanol-hexane to give the title compound (37 mg).

$^1$H NMR (300 MHz, DMSO-$d_6$) δ4.18 (2H, s), 6.89 (1H, d, J=6.8 Hz), 7.25 (1H, dd, J=9.0, 6.8 Hz), 7.32-7.38 (1H, m), 7.49-7.58 (2H, m), 7.61 (1H, d, J=1.5 Hz), 7.76 (1H, dd, J=12.1, 2.3 Hz), 7.87 (1H, s), 10.74 (1H, s).

Example 8

N-(3-fluoro-4-methoxyphenyl)-2-(imidazo[1,2-a]pyridin-5-yl)acetamide

A mixture of 2-(imidazo[1,2-a]pyridin-5-yl)acetic acid (50 mg), 3-fluoro-4-methoxyaniline (48 mg), HOBt monohydrate (44 mg), 1-ethyl-3-(3-dimethylaminopropyl)carbodiimide hydrochloride (82 mg), triethylamine (0.059 mL) and anhydrous DMF (1.0 mL) was stirred at room temperature overnight. The reaction mixture was purified by silica gel column chromatography (NH, ethyl acetate/methanol) to give the title compound (53 mg).

$^1$H NMR (300 MHz, DMSO-$d_6$) δ3.80 (3H, s), 4.12 (2H, s), 6.88 (1H, d, J=6.8 Hz), 7.07-7.18 (1H, m), 7.21-7.31 (2H, m), 7.50-7.59 (2H, m), 7.62 (1H, d, J=1.1 Hz), 7.87 (1H, s), 10.43 (1H, s).

Example 9

2-(imidazo[1,2-a]pyridin-5-yl)-N-(3,4,5-trifluorophenyl)acetamide

A mixture of 2-(imidazo[1,2-a]pyridin-5-yl)acetic acid (50 mg), 3,4,5-trifluoroaniline (50 mg), HOBt monohydrate (44 mg), 1-ethyl-3-(3-dimethylaminopropyl)carbodiimide hydrochloride (82 mg), triethylamine (0.059 mL) and anhydrous DMF (1.0 mL) was stirred at room temperature overnight. The reaction mixture was purified by silica gel column chromatography (NH, ethyl acetate/methanol) to give the title compound (44 mg).

$^1$H NMR (300 MHz, DMSO-$d_6$) δ4.18 (2H, s), 6.89 (1H, d, J=6.8 Hz), 7.25 (1H, dd, J=9.0, 6.8 Hz), 7.43-7.57 (3H, m), 7.62 (1H, d, J=1.5 Hz), 7.86 (1H, s), 10.77 (1H, s).

Example 10

2-(imidazo[1,2-a]pyridin-5-yl)-N-(4-propylphenyl)acetamide

To a mixture of 2-(imidazo[1,2-a]pyridin-5-yl)acetic acid (75 mg), 4-propylaniline (0.073 mL) and anhydrous DMF (2.8 mL) were added HATU (240 mg) and DIPEA (0.089 mL) at room temperature, and the mixture was stirred at room temperature for 3 days. The reaction mixture was diluted with saturated aqueous sodium hydrogen carbonate solution, and extracted with ethyl acetate. The extract was washed with water and saturated brine, and dried over anhydrous magnesium sulfate. The solvent was evaporated under reduced pressure and the obtained residue was purified by silica gel column chromatography (NH, ethyl acetate/methanol) and recrystallized from ethyl acetate-hexane to give the title compound (70 mg).

$^1$H NMR (300 MHz, DMSO-$d_6$) δ0.87 (3H, t, J=7.4 Hz), 1.45-1.64 (2H, m), 2.43-2.49 (2H, m), 4.12 (2H, s), 6.88 (1H, d, J=6.4 Hz), 7.12 (2H, d, J=8.5 Hz), 7.25 (1H, dd, J=9.1, 6.8 Hz), 7.41-7.57 (3H, m), 7.61 (1H, d, J=1.1 Hz), 7.87 (1H, s), 10.33 (1H, s).

Example 11

N-(4-ethyl-3-fluorophenyl)-2-(imidazo[1,2-a]pyridin-5-yl)acetamide (A) 2-fluoro-4-nitro-1-vinylbenzene A mixture of 1-bromo-2-fluoro-4-nitrobenzene (1.0 g), 2-vinylboronic acid pinacol ester (2.3 mL), tetrakis(triphenylphosphine)palladium(0) (530 mg), 2 M aqueous sodium carbonate solution (8.0 mL) and DMA (20 mL) was stirred under an argon gas atmosphere at 100° C. overnight. The obtained reaction mixture was diluted with water, and extracted with ethyl acetate. The extract was washed with water, and dried over anhydrous magnesium sulfate. The solvent was evaporated under reduced pressure and the obtained residue was purified by silica gel column chromatography (hexane/ethyl acetate) to give the title compound (0.76 g).

$^1$H NMR (300 MHz, CDCl$_3$) δ5.63 (1H, d, J=11.3 Hz), 6.02 (1H, d, J=17.7 Hz), 6.80-7.03 (1H, m), 7.56-7.76 (1H, m), 7.93 (1H, dd, J=10.2, 2.3 Hz), 8.01 (1H, dd, J=8.5, 2.1 Hz).

(B) 4-ethyl-3-fluoroaniline

A mixture of 2-fluoro-4-nitro-1-vinylbenzene (0.76 g), 10% Pd—C (0.50 g) and ethanol (30 mL) was stirred under a hydrogen gas atmosphere overnight. The insoluble material was filtered off and the filtrate was concentrated under reduced pressure to give the title compound (0.55 g).

$^1$H NMR (300 MHz, CDCl$_3$) δ1.17 (3H, t, J=7.5 Hz), 2.55 (2H, q, J=7.5 Hz), 3.47-3.76 (2H, m), 6.31-6.44 (2H, m), 6.88-7.00 (1H, m).

(C) N-(4-ethyl-3-fluorophenyl)-2-(imidazo[1,2-a]pyridin-5-yl)acetamide

A mixture of 2-(imidazo[1,2-a]pyridin-5-yl)acetic acid (50 mg), 4-ethyl-3-fluoroaniline (0.047 mL), HOBt monohydrate (44 mg), 1-ethyl-3-(3-dimethylaminopropyl)carbodiimide hydrochloride (82 mg), triethylamine (0.059 mL) and anhydrous DMF (1 mL) was stirred at room temperature overnight. The reaction mixture was purified by silica gel column chromatography (NH, ethyl acetate/methanol) to give the title compound (23 mg).

$^1$H NMR (300 MHz, DMSO-d$_6$) δ1.14 (3H, t, J=7.5 Hz), 2.52-2.62 (2H, m), 4.14 (2H, s), 6.88 (1H, d, J=6.4 Hz), 7.20-7.31 (3H, m), 7.46-7.57 (2H, m), 7.61 (1H, d, J=1.1 Hz), 7.86 (1H, s), 10.53 (1H, s).

Example 12

N-(4-cyclopropyl-3-fluorophenyl)-2-(imidazo[1,2-a]pyridin-5-yl)acetamide (A) tert-butyl (4-bromo-3-fluorophenyl)carbamate To 4-bromo-3-fluoroaniline (2.5 g) were added water (20 mL) and di-t-butyl dicarbonate (3.7 mL), and the mixture was stirred at room temperature for 3 days. Water (25 mL) was added, and the precipitated solid was collected by filtration, washed with water, and dried under reduced pressure to give the title compound (3.7 g).

$^1$H NMR (300 MHz, DMSO-d$_6$) δ1.48 (9H, s), 7.19 (1H, dd, J=8.7, 1.9 Hz), 7.43-7.65 (2H, m), 9.73 (1H, s).

(B) tert-butyl (4-cyclopropyl-3-fluorophenyl)carbamate

A mixture of tert-butyl (4-bromo-3-fluorophenyl)carbamate (500 mg), cyclopropylboronic acid (220 mg), tricyclohexylphosphine (190 mg), tripotassium phosphate (1800 mg), palladium(II) acetate (77 mg), water (5.0 mL) and toluene (5.0 mL) was stirred under microwave irradiation at 120° C. for 1 hr. The reaction mixture was extracted with ethyl acetate, and the obtained organic layer was washed with water and saturated brine, and dried over anhydrous sodium sulfate. The solvent was evaporated under reduced pressure and the obtained residue was purified by silica gel column chromatography (NH, hexane/ethyl acetate) to give the title compound (260 mg).

$^1$H NMR (300 MHz, DMSO-d$_6$) δ0.57-0.68 (2H, m), 0.82-0.96 (2H, m), 1.46 (9H, s), 1.85-1.97 (1H, m), 6.81-6.91 (1H, m), 7.09 (1H, dd, J=8.5, 2.1 Hz), 7.30 (1H, dd, J=13.2, 1.9 Hz), 9.43 (1H, s).

(C) N-(4-cyclopropyl-3-fluorophenyl)-2-(imidazo[1,2-a]pyridin-5-yl)acetamide

A mixture of tert-butyl (4-cyclopropyl-3-fluorophenyl)carbamate (86 mg) and 4 M hydrogen chloride ethyl acetate solution (1.0 mL) was stirred at room temperature overnight. The reaction mixture was concentrated under reduced pressure. To the obtained residue were added anhydrous DMF (2.0 mL), 2-(imidazo[1,2-a]pyridin-5-yl)acetic acid (50 mg), HATU (130 mg) and DIPEA (0.13 mL) at room temperature, and the mixture was stirred at room temperature for 3 days. The reaction mixture was diluted with water, and extracted with ethyl acetate. The extract was washed with water and saturated brine, and dried over anhydrous sodium sulfate. The solvent was evaporated under reduced pressure and the obtained residue was purified by silica gel column chromatography (ethyl acetate/methanol) and recrystallized from ethyl acetate-IPE to give the title compound (46 mg).

$^1$H NMR (300 MHz, DMSO-d$_6$) δ0.57-0.72 (2H, m), 0.84-0.99 (2H, m), 1.88-2.05 (1H, m), 4.14 (2H, s), 6.82-7.00 (2H, m), 7.13-7.30 (2H, m), 7.40-7.93 (4H, m), 10.52 (1H, s).

Example 13

N-(4-(2,2-difluoroethyl)phenyl)-2-(imidazo[1,2-a]pyridin-5-yl)acetamide (A) 4-(2,2-difluorovinyl)-N-(diphenylmethylene)aniline To a mixture of 1-bromo-4-(2,2-difluorovinyl)benzene (0.32 mL), 2-dicyclohexylphosphino-2',4',6'-triisopropyl-1,1'-biphenyl (220 mg), diphenylmethanimine (0.76 mL), sodium tert-butoxide (440 mg) and toluene (10 mL) was added tris(dibenzylideneacetone)dipalladium(0) (210 mg). The reaction mixture was stirred at 100° C. for 3 hr and cooled to room temperature. Water was added, and the mixture was extracted with ethyl acetate. The extract was washed with water and saturated brine, and dried over anhydrous sodium sulfate. The solvent was evaporated under reduced pressure and the obtained residue was purified by silica gel column chromatography (ethyl acetate/methanol) to give the title compound (790 mg).

MS: [M+H]$^+$ 320.2

(B) 4-(2,2-difluoroethyl)aniline

A mixture of 4-(2,2-difluorovinyl)-N-(diphenylmethylene)aniline (740 mg), 10% Pd—C (200 mg) and ethanol (20 mL) was stirred under a hydrogen gas atmosphere at room temperature overnight. The insoluble material was filtered off through celite, and the filtrate was concentrated under reduced pressure. The obtained residue was purified by silica gel column chromatography (hexane/ethyl acetate) to give the title compound (190 mg).

$^1$H NMR (300 MHz, DMSO-d$_6$) δ2.94 (2H, td, J=18.1, 4.5 Hz), 4.98 (2H, s), 5.81-6.32 (1H, m), 6.44-6.59 (2H, m), 6.91 (2H, d, J=8.3 Hz).

(C) N-(4-(2,2-difluoroethyl)phenyl)-2-(imidazo[1,2-a]pyridin-5-yl)acetamide

To a mixture of 2-(imidazo[1,2-a]pyridin-5-yl)acetic acid (50 mg) and anhydrous DMF (2.0 mL) were added 4-(2,2-difluoroethyl)aniline (54 mg), HATU (130 mg) and DIPEA (0.074 mL) at room temperature, and the mixture was stirred at room temperature overnight. The reaction mixture was diluted with water, and extracted with ethyl acetate. The extract was washed with water and saturated brine, and dried over anhydrous sodium sulfate. The solvent was evaporated under reduced pressure and the obtained residue was purified by silica gel column chromatography (NH, ethyl acetate/methanol) and recrystallized from ethyl acetate-IPE to give the title compound (44 mg).

$^1$H NMR (300 MHz, DMSO-d$_6$) δ3.12 (2H, td, J=18.2, 4.3 Hz), 4.14 (2H, s), 5.95-6.45 (1H, m), 6.89 (1H, d, J=6.8 Hz), 7.17-7.32 (3H, m), 7.48-7.58 (3H, m), 7.61 (1H, d, J=1.1 Hz), 7.87 (1H, s), 10.43 (1H, s).

Example 14

N-(3-fluoro-4-(trifluoromethoxy)phenyl)-2-(imidazo[1,2-a]pyridin-5-yl) acetamide To a mixture of 3-fluoro-4-(trifluoromethoxy)aniline (66 mg), 2-(imidazo[1,2-a]pyridin-5-yl)acetic acid (50 mg) and anhydrous DMF (1 mL) were added HATU (160 mg) and DIPEA (0.074 mL) at room temperature, and the mixture was stirred at room temperature for 3 days. The reaction mixture was diluted with saturated aqueous sodium hydrogen carbonate solution, and extracted with ethyl acetate. The extract was washed with water and saturated brine, and dried over anhydrous magnesium sulfate. The solvent was evaporated under reduced pressure and the obtained residue was purified by silica gel column chromatography (NH, ethyl acetate/methanol) and recrystallized from ethyl acetate-hexane to give the title compound (63 mg). $^1$H NMR (300 MHz, CDCl$_3$) δ3.98 (2H, s), 6.82 (1H, d, J=6.8 Hz), 7.08-7.24 (3H, m), 7.52 (1H, s), 7.58 (1H, d, J=9.0 Hz), 7.61-7.74 (2H, m), 8.12 (1H, brs).

Example 15

N-(3-fluoro-4-methylphenyl)-2-(imidazo[1,2-a]pyridin-5-yl)acetamide

To a mixture of 2-(imidazo[1,2-a]pyridin-5-yl)acetic acid (50 mg) and anhydrous DMF (2.0 mL) were added 3-fluoro-4-methylaniline (0.039 mL), HATU (130 mg) and DIPEA (0.074 mL) at room temperature, and the mixture was stirred at room temperature overnight. The reaction mixture was diluted with water, and extracted with ethyl acetate. The extract was washed with water and saturated brine, and dried over anhydrous sodium sulfate. The solvent was evaporated under reduced pressure, and the obtained residue was purified by NH silica gel column chromatography (ethyl acetate/methanol) and recrystallized from ethyl acetate-hexane to give the title compound (45 mg).
$^1$H NMR (300 MHz, DMSO-d$_6$) δ2.17 (3H, d, J=1.5 Hz), 4.14 (2H, s), 6.88 (1H, d, J=6.8 Hz), 7.16-7.30 (3H, m), 7.46-7.58 (2H, m), 7.61 (1H, d, J=1.1 Hz), 7.87 (1H, s), 10.52 (1H, s).

Example 16

2-(imidazo[1,2-a]pyridin-5-yl)-N-(4-iodophenyl)acetamide

To a mixture of 4-iodoaniline (300 mg), 2-(imidazo[1,2-a]pyridin-5-yl)acetic acid (200 mg) and anhydrous DMF (8.0 mL) were added HATU (520 mg) and DIPEA (0.30 mL) at room temperature, and the mixture was stirred at room temperature overnight. The reaction mixture was diluted with water, and extracted with ethyl acetate. The extract was washed with water and saturated brine, and dried over anhydrous sodium sulfate. The solvent was evaporated under reduced pressure, and the obtained residue was purified by silica gel column chromatography (NH, ethyl acetate/methanol) and recrystallized from ethyl acetate-IPE to give the title compound (290 mg). $^1$H NMR (300 MHz, DMSO-d$_6$) δ4.15 (2H, s), 6.88 (1H, d, J=6.8 Hz), 7.25 (1H, dd, J=9.0, 6.8 Hz), 7.38-7.48 (2H, m), 7.54 (1H, d, J=9.0 Hz), 7.59-7.72 (3H, m), 7.87 (1H, s), 10.52 (1H, s).

Example 17

N-(4-(difluoromethoxy)-3-fluorophenyl)-2-(imidazo[1,2-a]pyridin-5-yl)acetamide

To a mixture of 4-(difluoromethoxy)-3-fluoroaniline (100 mg), 2-(imidazo[1,2-a]pyridin-5-yl)acetic acid (79 mg) and anhydrous DMF (3.0 mL) were added HATU (260 mg) and DIPEA (0.094 mL) at room temperature, and the mixture was stirred at room temperature overnight. The reaction mixture was diluted with saturated aqueous sodium hydrogen carbonate solution, and extracted with ethyl acetate. The extract was washed with water and saturated brine, dried over anhydrous magnesium sulfate. The solvent was evaporated under reduced pressure and the obtained residue was purified by silica gel column chromatography (NH, ethyl acetate/methanol) and recrystallized from THF-hexane to give the title compound (110 mg).
$^1$H NMR (300 MHz, DMSO-d$_6$) δ4.17 (2H, s), 6.87-6.96 (1H, m), 7.16 (1H, s), 7.20-7.45 (3H, m), 7.55 (1H, d, J=9.1 Hz), 7.62 (1H, d, J=1.3 Hz), 7.69-7.80 (1H, m), 7.83-7.92 (1H, m), 10.68 (1H, s).

Example 18

N-(4-ethoxy-3-fluorophenyl)-2-(imidazo[1,2-a]pyridin-5-yl)acetamide (A) 1-ethoxy-2-fluoro-4-nitrobenzene To a mixture of 2-fluoro-4-nitrophenol (1.0 g), cesium carbonate (4.2 g) and DMF (6.4 mL) was added iodoethane (1.0 mL), and the mixture was stirred at 60° C. for 2 hr. The reaction mixture was diluted with water, and extracted with ethyl acetate. The extract was washed with water and saturated brine, and dried over anhydrous sodium sulfate. The solvent was evaporated under reduced pressure, and the obtained residue was purified by silica gel column chromatography (hexane/ethyl acetate) to give the title compound (1.1 g).
$^1$H NMR (300 MHz, CDCl$_3$) δ1.44-1.58 (3H, m), 4.22 (2H, q, J=7.0 Hz), 6.94-7.08 (1H, m), 7.92-8.12 (2H, m).

(B) 4-ethoxy-3-fluoroaniline

A mixture of 1-ethoxy-2-fluoro-4-nitrobenzene (260 mg) and 10% Pd—C (100 mg) and ethanol (10 mL) was stirred under a hydrogen gas atmosphere at room temperature overnight. The insoluble material was filtered off through celite, and the filtrate was concentrated under reduced pressure to give the title compound (210 mg).
$^1$H NMR (300 MHz, DMSO-d$_6$) δ1.25 (3H, t, J=7.0 Hz), 3.91 (2H, q, J=6.8 Hz), 4.90 (2H, s), 6.28 (1H, ddd, J=8.7, 2.6, 1.1 Hz), 6.38 (1H, dd, J=13.6, 2.6 Hz), 6.73-6.87 (1H, m).

(C) N-(4-ethoxy-3-fluorophenyl)-2-(imidazo[1,2-a]pyridin-5-yl)acetamide

To a mixture of 4-ethoxy-3-fluoroaniline (66 mg), 2-(imidazo[1,2-a]pyridin-5-yl)acetic acid (50 mg) and anhydrous DMF (2 mL) were added HATU (130 mg) and DIPEA (0.074 mL) at room temperature, and the mixture was stirred at room temperature overnight. The reaction mixture was diluted with water, and extracted with ethyl acetate. The extract was washed with water and saturated brine, and dried over anhydrous sodium sulfate. The solvent was evaporated under reduced pressure, and the obtained residue was purified by silica gel column chromatography (NH, ethyl acetate/methanol) and recrystallized from ethyl acetate-hexane to give the title compound (43 mg).
$^1$H NMR (300 MHz, DMSO-d$_6$) δ1.32 (3H, t, J=7.0 Hz), 4.05 (2H, q, J=6.8 Hz), 4.12 (2H, s), 6.88 (1H, d, J=6.8 Hz), 7.04-7.17 (1H, m), 7.19-7.30 (2H, m), 7.49-7.60 (2H, m), 7.62 (1H, d, J=1.1 Hz), 7.87 (1H, s), 10.43 (1H, s).

Example 19

N-(3,5-difluoro-4-methoxyphenyl)-2-(imidazo[1,2-a]pyridin-5-yl)acetamide

To a mixture of 3,5-difluoro-4-methoxyaniline (54 mg), 2-(imidazo[1,2-a]pyridin-5-yl)acetic acid (50 mg) and anhydrous DMF (1 mL) were added HATU (160 mg) and DIPEA (0.074 mL) at room temperature, and the mixture was stirred at room temperature for 3 days. The reaction mixture was diluted with saturated aqueous sodium hydrogen carbonate solution, and extracted with ethyl acetate. The extract was washed with water and saturated brine, and dried over anhydrous magnesium sulfate. The solvent was evaporated under reduced pressure and the obtained residue was purified by silica gel column chromatography (NH, ethyl acetate/methanol) and recrystallized from ethyl acetate-hexane to give the title compound (46 mg). $^1$H NMR (300 MHz, DMSO-$d_6$) δ3.86 (3H, s), 4.15 (2H, s), 6.88 (1H, d, J=6.8 Hz), 7.25 (1H, dd, J=9.0, 6.8 Hz), 7.35 (2H, d, J=10.5 Hz), 7.55 (1H, d, J=9.0 Hz), 7.62 (1H, d, J=1.1 Hz), 7.85 (1H, s), 10.66 (1H, s).

Example 20

2-(3-methylimidazo[1,2-a]pyridin-5-yl)-N-(4-(trifluoromethyl)phenyl)acetamide (A) 5-bromo-3-methylimidazo[1,2-a]pyridine hydrobromide A solution of 6-bromopyridin-2-amine (2.0 g) and 2-bromo-1,1-diethoxypropane (3.3 mL) in ethanol (30 mL) was heated under reflux for 15 hr. 2-Bromo-1,1-diethoxypropane (1.6 mL) was further added, and the reaction mixture was heated under reflux for 10 hr. After cooling to room temperature, the precipitate was collected by filtration and washed with ethanol to give the title compound (2.7 g). The filtrate was diluted with IPE, and the obtained precipitate was collected by filtration and washed with a mixed solvent of ethanol-IPE to give the title compound (0.30 g).
$^1$H NMR (300 MHz, DMSO-$d_6$) δ2.88 (3H, s), 7.62-7.76 (2H, m), 7.90 (1H, dd, J=8.5, 1.7 Hz), 8.02 (1H, s).

(B) 5-bromo-3-methylimidazo[1,2-a]pyridine

5-Bromo-3-methylimidazo[1,2-a]pyridine hydrobromide (1.0 g) was treated with saturated aqueous sodium hydrogen carbonate solution, and the mixture was extracted with ethyl acetate. The organic layer was washed with saturated brine, and dried over anhydrous magnesium sulfate. The solvent was evaporated under reduced pressure to give the title compound (0.72 g). $^1$H NMR (300 MHz, CDCl$_3$) δ2.86 (3H, s), 6.86-7.00 (2H, m), 7.36 (1H, s), 7.47-7.57 (1H, m).

(C) tert-butyl 2-(3-methylimidazo[1,2-a]pyridin-5-yl)acetate

To a mixture of 5-bromo-3-methylimidazo[1,2-a]pyridine (200 mg), bis(dibenzylideneacetone)palladium (11 mg), 1,2,3,4,5-pentaphenyl-1'-(di-t-butylphosphino)ferrocene (13 mg) and dry THF (3 mL) was added a 0.5 M diethyl ether solution (2.3 mL) of tert-butoxy-2-oxoethylzinc chloride at room temperature. Under a nitrogen atmosphere, the reaction mixture was stirred at 80° C. overnight. The mixture was cooled to room temperature, diluted with water, and extracted with ethyl acetate. The organic layer was washed with saturated brine, and dried over anhydrous magnesium sulfate. The solvent was evaporated under reduced pressure and the obtained residue was purified by silica gel column chromatography (NH, hexane/ethyl acetate) to give the title compound (54 mg).
$^1$H NMR (300 MHz, CDCl$_3$) δ1.44 (9H, s), 2.71 (3H, s), 4.07 (2H, s), 6.51-6.59 (1H, m), 7.03 (1H, dd, J=9.2, 6.6 Hz), 7.33 (1H, s), 7.44-7.56 (1H, m).

(D) 2-(3-methylimidazo[1,2-a]pyridin-5-yl)-N-(4-(trifluoromethyl)phenyl)acetamide A solution of tert-butyl 2-(3-methylimidazo[1,2-a]pyridin-5-yl)acetate (53 mg) in trifluoroacetic acid (1.5 mL) was stirred at 0° C. for 1 hr and then at room temperature for 3 hr. The reaction mixture was concentrated under reduced pressure to give 2-(3-methylimidazo[1,2-a]pyridin-5-yl)acetic acid trifluoroacetate (66 mg). To the obtained 2-(3-methylimidazo[1,2-a]pyridin-5-yl)acetic acid trifluoroacetate were added anhydrous DMF (1 mL), 4-(trifluoromethyl)aniline (0.082 mL), HATU (250 mg) and DIPEA (0.15 mL), and the mixture was stirred at room temperature overnight. The reaction mixture was diluted with saturated aqueous sodium hydrogen carbonate solution, and extracted with ethyl acetate. The extract was washed with water and saturated brine, and dried over anhydrous magnesium sulfate. The solvent was evaporated under reduced pressure and the obtained residue was purified by silica gel column chromatography (NH, ethyl acetate/methanol) and recrystallized from methanol-IPE to give the title compound (30 mg).
$^1$H NMR (300 MHz, CDCl$_3$) δ 2.73 (3H, s), 4.27 (2H, s), 6.61-6.77 (1H, m), 7.08 (1H, dd, J=9.2, 6.6 Hz), 7.35 (1H, s), 7.44-7.68 (5H, m), 7.88 (1H, brs).

Example 60

2-([1,2,4]triazolo[1,5-a]pyridin-5-yl)-N-(4-(trifluoromethyl)phenyl)acetamide (A) tert-butyl 2-([1,2,4]triazolo[1,5-a]pyridin-5-yl)acetate To a mixture of zinc powder (190 mg) and dry THF (5.4 mL) was added chlorotrimethylsilane (0.019 mL) under a nitrogen atmosphere, and the mixture was stirred at room temperature for 1 hr. To the reaction mixture was added tert-butyl bromoacetate (0.22 mL) at room temperature, and the mixture was heated at 40° C. for 1 hr. Furthermore, 5-chloro-[1,2,4]triazolo[1,5-a]pyridine (100 mg), bis(dibenzylideneacetone)palladium (37 mg) and 1,2,3,4,5-pentaphenyl-1'-(di-t-butylphosphino)ferrocene (23 mg) were added at room temperature. The reaction mixture was heated at 80° C. for 20 hr. The reaction mixture was cooled to room temperature, diluted with water and saturated brine, and extracted with ethyl acetate. The extract was dried over anhydrous magnesium sulfate and the solvent was evaporated under reduced pressure. The obtained residue was purified by silica gel column chromatography (NH, hexane/ethyl acetate) to give the title compound (42 mg).
$^1$H NMR (300 MHz, DMSO-$d_6$) δ1.37 (9H, s), 4.18 (2H, s), 7.19 (1H, d, J=6.41 Hz), 7.60-7.71 (1H, m), 7.77-7.86 (1H, m), 8.49 (1H, s).

(B) 2-([1,2,4]triazolo[1,5-a]pyridin-5-yl)-N-(4-(trifluoromethyl)phenyl)acetamide To tert-butyl 2-([1,2,4]triazolo[1,5-a]pyridin-5-yl)acetate (42 mg) was added trifluoroacetic acid (1.2 mL) at 0° C. The reaction mixture was stirred at room temperature for 1 day. The reaction mixture was concentrated under reduced pressure, toluene was added to the residue and the mixture was concentrated again. To the obtained residue were added anhydrous DMF (0.9 mL), 4-(trifluoromethyl)aniline (0.068 mL), HATU (270 mg) and DIPEA (0.19 mL), and the mixture was stirred at room temperature for 20 hr. To the reaction mixture were added water, saturated aqueous sodium hydrogen carbonate solution, and saturated brine, and the mixture was extracted with ethyl acetate. The extract was dried over anhydrous magnesium sulfate and the solvent was evaporated under reduced pressure. The obtained residue was purified by silica gel column chromatography (NH, hexane/ethyl acetate) and recrystallized from ethyl acetate-hexane to give the title compound (29 mg).

$^1$H NMR (300 MHz, DMSO-d$_6$) δ4.37 (2H, s), 7.24 (1H, d, J=7.16 Hz), 7.64-7.74 (3H, m), 7.76-7.86 (3H, m), 8.48 (1H, s), 10.79 (1H, s).

The compounds of Examples 21-59 and 61-77 in the following Tables were produced according to the methods shown in the above-mentioned Examples, or a method analogous thereto. The Example compounds are shown in the following Tables. In the Tables, MS shows measured values.

TABLE 1-1

| Ex. No. | IUPAC name | Structure | Salt | MS |
|---|---|---|---|---|
| 1 | 2-(imidazo[1,2-a]pyridin-5-yl)-N-(4-(trifluoromethyl)phenyl)-acetamide | 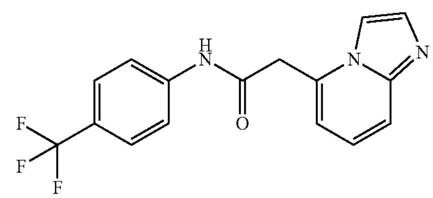 | | 317.9 |
| 2 | 2-(imidazo[1,2-a]pyridin-5-yl)-N-(4-methoxyphenyl)acetamide | 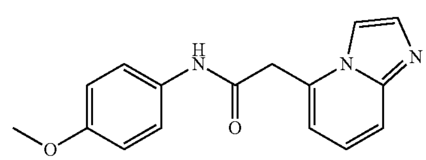 [SMILES: COc1ccc(NC(=O)Cc2cccc3nccn23)cc1] | | 282.2 |
| 3 | N-(4-ethylphenyl)-2-(imidazo[1,2-a]pyridin-5-yl)acetamide | 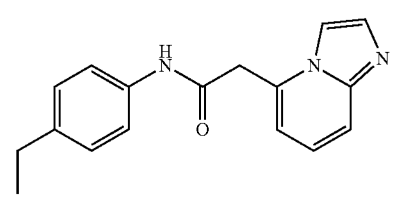 [SMILES: CCc1ccc(NC(=O)Cc2cccc3nccn23)cc1] | | 280.2 |
| 4 | N-(4-cyclopropylphenyl)-2-(imidazo[1,2-a]pyridin-5-yl)acetamide | 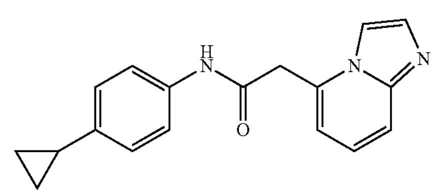 [SMILES: O=C(Cc1cccc2nccn12)Nc1ccc(C2CC2)cc1] | | 292.2 |
| 5 | 2-(imidazo[1,2-a]pyridin-5-yl)-N-(4-(trifluoromethoxy)-phenyl)acetamide | 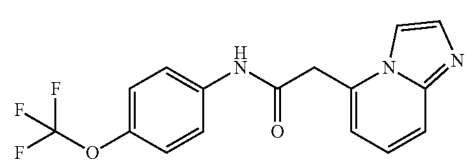 | | 336.1 |
| 6 | N-(4-(difluoromethoxy)phenyl)-2-(imidazo[1,2-a]pyridin-5-yl)acetamide | 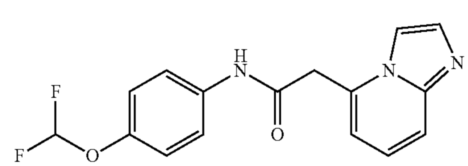 | | 318.1 |

TABLE 1-2

| Ex. No. | IUPAC name | Structure | Salt | MS |
|---|---|---|---|---|
| 7 | N-(4-chloro-3-fluorophenyl)-2-(imidazo[1,2-a]pyridin-5-yl)acetamide | 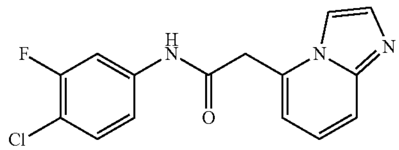 [SMILES: O=C(Cc1cccc2nccn12)Nc1ccc(Cl)c(F)c1] | | 304.1 |
| 8 | N-(3-fluoro-4-methoxyphenyl)-2-(imidazo[1,2-a]pyridin-5-yl)acetamide | 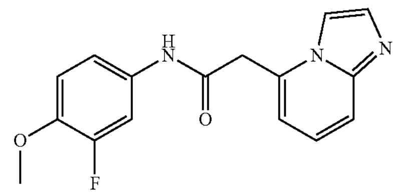 [SMILES: COc1ccc(NC(=O)Cc2cccc3nccn23)cc1F] | | 300.2 |
| 9 | 2-(imidazo[1,2-a]pyridin-5-yl)-N-(3,4,5-trifluorophenyl)acetamide | 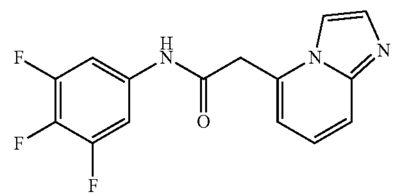 [SMILES: O=C(Cc1cccc2nccn12)Nc1cc(F)c(F)c(F)c1] | | 303.9 |
| 10 | 2-(imidazo[1,2-a]pyridin-5-yl)-N-(4-propylphenyl)acetamide | 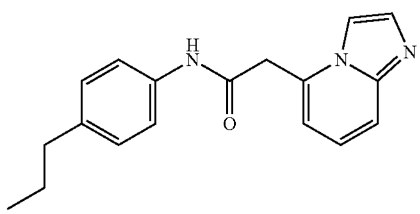 [SMILES: CCCc1ccc(NC(=O)Cc2cccc3nccn23)cc1] | | 294.1 |
| 11 | N-(4-ethyl-3-fluorophenyl)-2-(imidazo[1,2-a]pyridin-5-yl)acetamide | 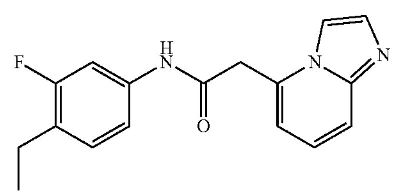 [SMILES: CCc1ccc(NC(=O)Cc2cccc3nccn23)cc1F] | | 298.2 |
| 12 | N-(4-cyclopropyl-3-fluorophenyl)-2-(imidazo[1,2-a]pyridin-5-yl)acetamide | 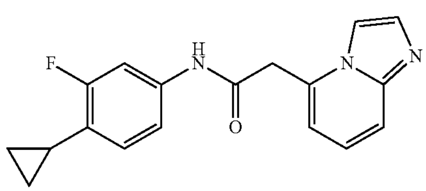 [SMILES: O=C(Cc1cccc2nccn12)Nc1ccc(C2CC2)c(F)c1] | | 310.2 |

TABLE 1-3

| Ex. No. | IUPAC name | Structure | Salt | MS |
|---|---|---|---|---|
| 13 | N-(4-(2,2-difluoroethyl)phenyl)-2-(imidazo[1,2-a]pyridin-5-yl)acetamide | 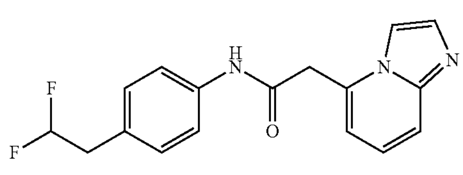 [SMILES: O=C(Cc1cccc2nccn12)Nc1ccc(CC(F)F)cc1] | | 316.1 |

TABLE 1-3-continued

| Ex. No. | IUPAC name | Structure | Salt | MS |
|---|---|---|---|---|
| 14 | N-(3-fluoro-4-(trifluoromethoxy)-phenyl)-2-(imidazo[1,2-a]pyridin-5-yl)acetamide | 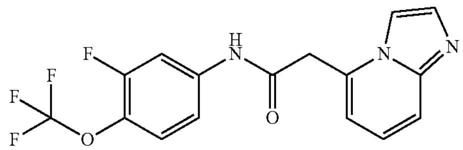 [SMILES: O=C(Cc1cccc2nccn12)Nc1ccc(OC(F)(F)F)c(F)c1] | | 354.1 |
| 15 | N-(3-fluoro-4-methylphenyl)-2-(imidazo[1,2-a]pyridin-5-yl)acetamide | 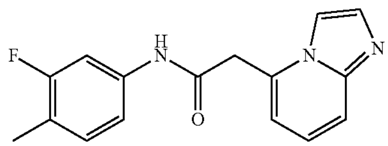 [SMILES: Cc1ccc(NC(=O)Cc2cccc3nccn23)cc1F] | | 284.2 |
| 16 | 2-{imidazo[1,2-a]pyridin-5-yl}-N-(4-iodophenyl)acetamide | 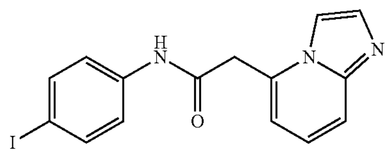 [SMILES: O=C(Cc1cccc2nccn12)Nc1ccc(I)cc1] | | 378.0 |
| 17 | N-{4-(difluoromethoxy)-3-fluorophenyl)-2-(imidazo[1,2-a]pyridin-5-yl)acetamide | 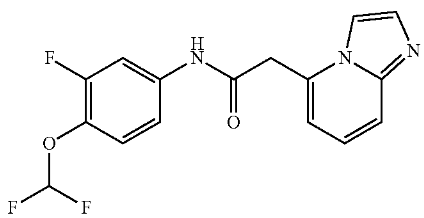 [SMILES: O=C(Cc1cccc2nccn12)Nc1ccc(OC(F)F)c(F)c1] | | 333.9 |
| 18 | N-(4-ethoxy-3-fluorophenyl)-2-(imidazo[1,2-a]pyridin-5-yl)acetamide | 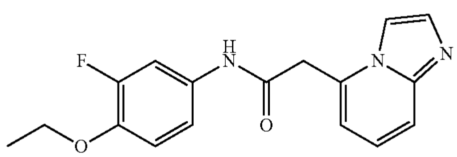 [SMILES: CCOc1ccc(NC(=O)Cc2cccc3nccn23)cc1F] | | 314.2 |

TABLE 1-4

| Ex. No. | IUPAC name | Structure | Salt | MS |
|---|---|---|---|---|
| 19 | N-(3,5-difluoro-4-methoxyphenyl)-2-(imidazo[1,2-a]pyridin-5-yl)acetamide | 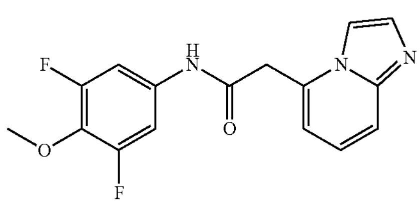 [SMILES: COc1c(F)cc(NC(=O)Cc2cccc3nccn23)cc1F] | | 315.9 |
| 20 | 2-(3-methylimidazo[1,2-a]pyridin-5-yl)-N-(4-(trifluoromethyl)phenyl)-acetamide | 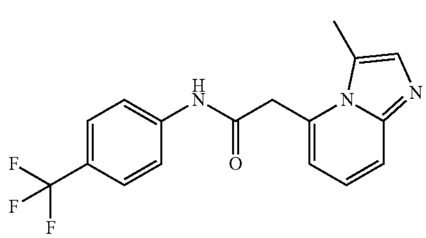 [SMILES: Cc1cnc2cccc(CC(=O)Nc3ccc(C(F)(F)F)cc3)n12] | | 334.0 |

TABLE 1-4-continued

| Ex. No. | IUPAC name | Structure | Salt | MS |
|---|---|---|---|---|
| 21 | N-(3-(difluoromethyl)-4-fluorophenyl)-2-(imidazo[1,2-a]pyridin-5-yl)acetamide | 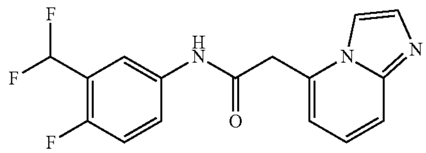 [SMILES: O=C(Cc1cccc2nccn12)Nc1ccc(F)c(C(F)F)c1] | | 320.0 |
| 22 | 2-(8-methylimidazo[1,2-a]pyridin-5-yl)-N-(4-(trifluoromethyl)phenyl)acetamide | 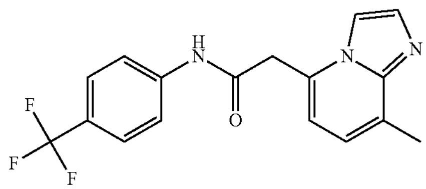 [SMILES: Cc1ccc(CC(=O)Nc2ccc(C(F)(F)F)cc2)n2ccnc12] | | 334.1 |
| 23 | 2-(2-methylimidazo[1,2-a]pyridin-5-yl)-N-(4-(trifluoromethyl)phenyl)acetamide | 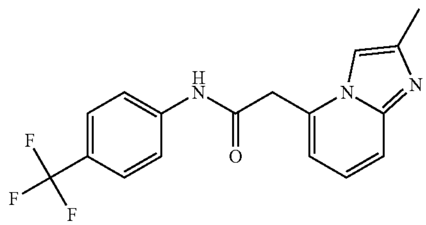 [SMILES: Cc1cn2c(CC(=O)Nc3ccc(C(F)(F)F)cc3)cccc2n1] | | 334.1 |
| 24 | 2-(imidazo[1,2-a]pyridin-5-yl)-N-(6-methoxypyridin-3-yl)acetamide | 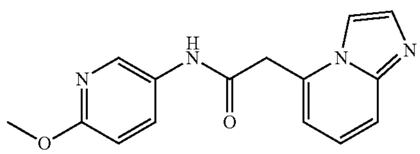 [SMILES: COc1ccc(NC(=O)Cc2cccc3nccn23)cn1] | | 283.1 |

TABLE 1-5

| Ex. No. | IUPAC name | Structure | Salt | MS |
|---|---|---|---|---|
| 25 | 2-(imidazo[1,2-a]pyridin-5-yl)-N-(5-methylpyridin-2-yl)acetamide | 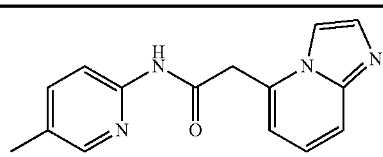 | | 267.2 |
| 26 | 2-(imidazo[1,2-a]pyridin-5-yl)-N-phenylacetamide | 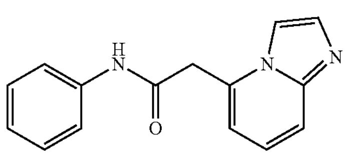 [SMILES: O=C(Cc1cccc2nccn12)Nc1ccccc1] | | 252.2 |
| 27 | N-(2,4-difluorophenyl)-2-(imidazo[1,2-a]pyridin-5-yl)acetamide | 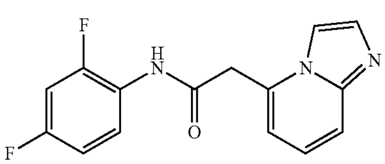 [SMILES: O=C(Cc1cccc2nccn12)Nc1ccc(F)cc1F] | | 288.1 |
| 28 | 2-(imidazo[1,2-a]pyridin-5-yl)-N-(2-methylphenyl)acetamide | 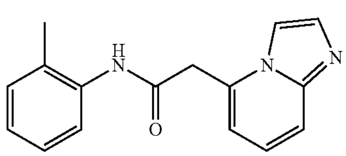 [SMILES: Cc1ccccc1NC(=O)Cc1cccc2nccn12] | | 266.2 |

TABLE 1-5-continued

| Ex. No. | IUPAC name | Structure | Salt | MS |
|---|---|---|---|---|
| 29 | N-(3,4-difluorophenyl)-2-(imidazo[1,2-a]pyridin-5-yl)acetamide | 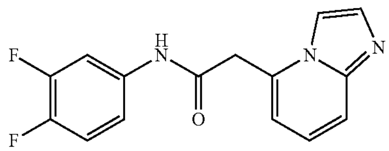 [SMILES: O=C(Cc1cccc2nccn12)Nc1ccc(F)c(F)c1] | | 288.1 |
| 30 | 2-(imidazo[1,2-a]pyridin-5-yl)-N-(3-methylphenyl)acetamide | 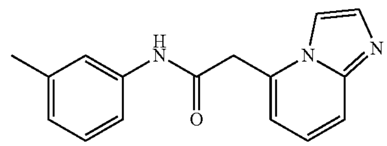 [SMILES: Cc1cccc(NC(=O)Cc2cccc3nccn23)c1] | | 266.2 |

TABLE 1-6

| Ex. No. | IUPAC name | Structure | Salt | MS |
|---|---|---|---|---|
| 31 | N-(4-cyanophenyl)-2-(imidazo[1,2-a]pyridin-5-yl)acetamide | 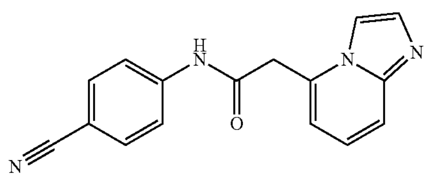 [SMILES: N#Cc1ccc(NC(=O)Cc2cccc3nccn23)cc1] | | 277.1 |
| 32 | N-(4-fluorophenyl)-2-(imidazo[1,2-a]pyridin-5-yl)acetamide | 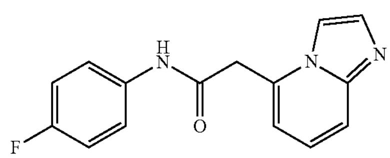 [SMILES: O=C(Cc1cccc2nccn12)Nc1ccc(F)cc1] | | 270.1 |
| 33 | N-(4-chlorophenyl)-2-(imidazo[1,2-a]pyridin-5-yl)acetamide | 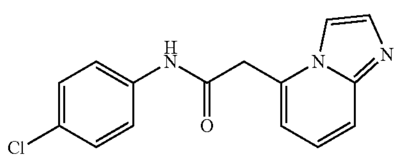 [SMILES: O=C(Cc1cccc2nccn12)Nc1ccc(Cl)cc1] | | 286.0 |
| 34 | 2-(imidazo[1,2-a]pyridin-5-yl)-N-(4-phenoxyphenyl)acetamide | 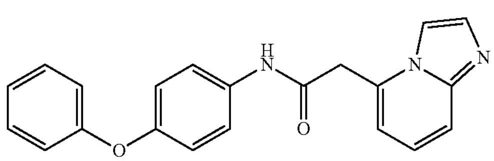 [SMILES: O=C(Cc1cccc2nccn12)Nc1ccc(Oc2ccccc2)cc1] | | 344.1 |
| 35 | 2-(imidazo[1,2-a]pyridin-5-yl)-N-(4-methylphenyl)acetamide | 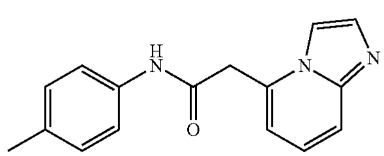 [SMILES: Cc1ccc(NC(=O)Cc2cccc3nccn23)cc1] | | 266.2 |
| 36 | 2-(imidazo[1,2-a]pyridin-5-yl)-N-(5-(trifluoromethyl)pyridin-2-yl)acetamide | 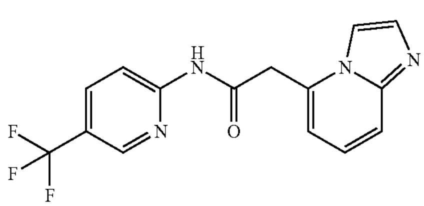 [SMILES: O=C(Cc1cccc2nccn12)Nc1ccc(C(F)(F)F)cn1] | | 321.1 |

TABLE 1-7

| Ex. No. | IUPAC name | Structure | Salt | MS |
|---|---|---|---|---|
| 37 | N-(2-chloro-4-(trifluoromethyl)phenyl)-2-(imidazo[1,2-a]pyridin-5-yl)acetamide | 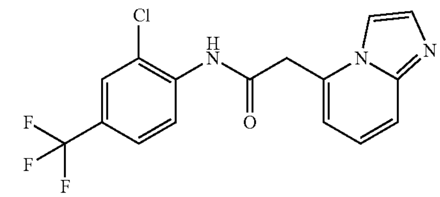 [SMILES: O=C(Cc1cccc2nccn12)Nc1ccc(C(F)(F)F)cc1Cl] | | 354.0 |
| 38 | 2-(imidazo[1,2-a]pyridin-5-yl)-N-(4-(2,2,2-trifluoroethoxy)phenyl)-acetamide | 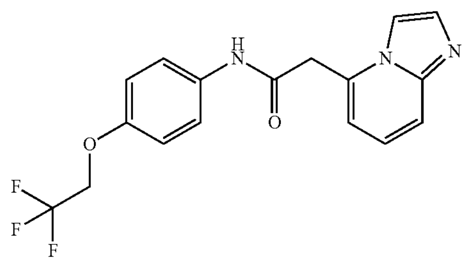 [SMILES: O=C(Cc1cccc2nccn12)Nc1ccc(OCC(F)(F)F)cc1] | | 350.1 |
| 39 | N-(3-chloro-4-(trifluoromethyl)phenyl)-2-(imidazo[1,2-a]pyridin-5-yl)acetamide | 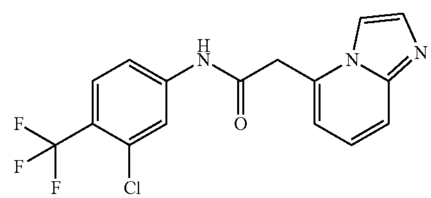 [SMILES: O=C(Cc1cccc2nccn12)Nc1ccc(C(F)(F)F)c(Cl)c1] | | 354.0 |
| 40 | 2-(imidazo[1,2-a]pyridin-5-yl)-N-(5-methylpyrimidin-2-yl)acetamide | 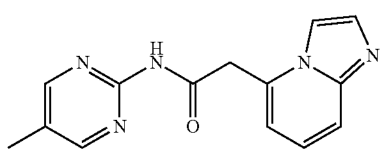 [SMILES: Cc1cnc(NC(=O)Cc2cccc3nccn23)nc1] | | 268.1 |
| 41 | 4-((imidazo[1,2-a]pyridin-5-ylacetyl)amino)-N,N-dimethylbenzamide | 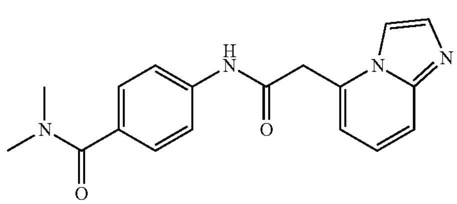 [SMILES: CN(C)C(=O)c1ccc(NC(=O)Cc2cccc3nccn23)cc1] | | 323.2 |
| 42 | 2-(imidazo[1,2-a]pyridin-5-yl)-N-(6-methylpyridin-3-yl)acetamide | 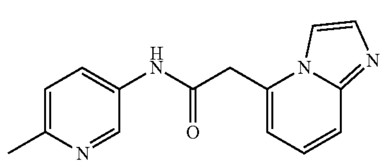 [SMILES: Cc1ccc(NC(=O)Cc2cccc3nccn23)cn1] | | 267.2 |

TABLE 1-8

| Ex. No. | IUPAC name | Structure | Salt | MS |
|---|---|---|---|---|
| 43 | N-(2-fluoro-4-(trifluoromethyl)phenyl)-2-(imidazo[1,2-a]pyridin-5-yl)acetamide | 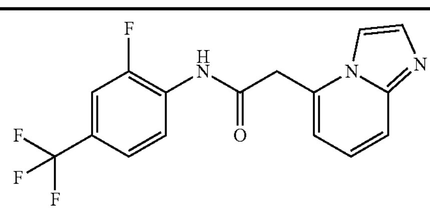 | | 338.1 |

TABLE 1-8-continued

| Ex. No. | IUPAC name | Structure | Salt | MS |
|---|---|---|---|---|
| 44 | 2-(imidazo[1,2-a]pyridin-5-yl)-N-(6-(trifluoromethyl)pyridin-3-yl)acetamide | 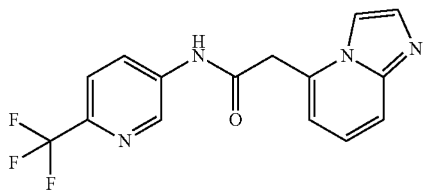 [SMILES: O=C(Cc1cccc2nccn12)Nc1ccc(C(F)(F)F)nc1] | | 321.1 |
| 45 | 2-(imidazo[1,2-a]pyridin-5-yl)-N-(2-methoxypyrimidin-5-yl)acetamide | 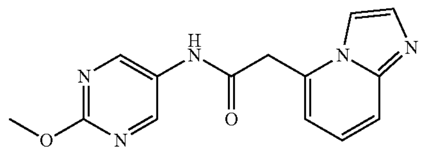 [SMILES: COc1ncc(NC(=O)Cc2cccc3nccn23)cn1] | | 284.2 |
| 46 | 2-(imidazo[1,2-a]pyridin-5-yl)-N-(5-methylpyrazin-2-yl)acetamide | 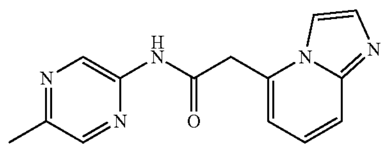 [SMILES: Cc1cnc(NC(=O)Cc2cccc3nccn23)cn1] | | 268.1 |
| 47 | 2-(imidazo[1,2-a]pyridin-5-yl)-N-(2-(trifluoromethyl)-pyrimidin-5-yl)acetamide | 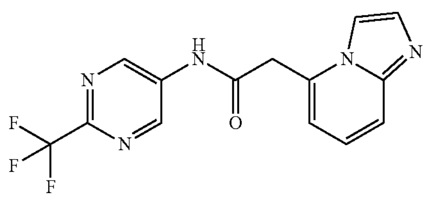 [SMILES: O=C(Cc1cccc2nccn12)Nc1cnc(C(F)(F)F)nc1] | | 322.2 |
| 48 | N-(5-cyclopropyl-1,3,4-thiadiazol-2-yl)-2-(imidazo[1,2-a]pyridin-5-yl)acetamide | 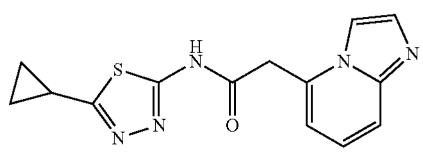 [SMILES: O=C(Cc1cccc2nccn12)Nc1nnc(C2CC2)s1] | | 300.2 |

TABLE 1-9

| Ex. No. | IUPAC name | Structure | Salt | MS |
|---|---|---|---|---|
| 49 | 2-(imidazo[1,2-a]pyridin-5-yl)-N-(1-methyl-1H-pyrazol-5-yl)acetamide | 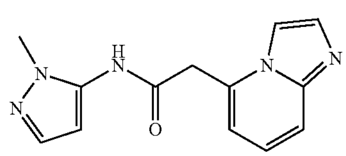 [SMILES: Cn1nccc1NC(=O)Cc1cccc2nccn12] | | 256.1 |
| 50 | 2-(imidazo[1,2-a]pyridin-5-yl)-N-(1-methyl-1H-pyrazol-3-yl)acetamide | 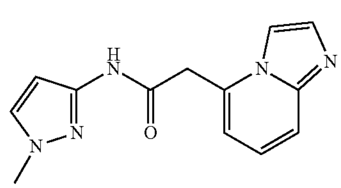 [SMILES: Cn1ccc(NC(=O)Cc2cccc3nccn23)n1] | | 256.1 |

TABLE 1-9-continued

| Ex. No. | IUPAC name | Structure | Salt | MS |
|---|---|---|---|---|
| 51 | 2-(imidazo[1,2-a]pyridin-5-yl)-N-methyl-N-(4-(trifluoromethyl)phenyl)-acetamide | 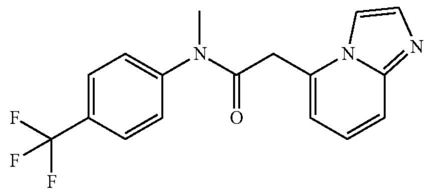 [SMILES: CN(C(=O)Cc1cccc2nccn12)c1ccc(C(F)(F)F)cc1] | | 334.2 |
| 52 | 2-(imidazo[1,2-a]pyridin-5-yl)-N-(4-(trifluoromethyl)-cyclohexyl)acetamide | 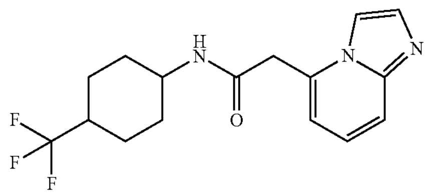 [SMILES: O=C(Cc1cccc2nccn12)NC1CCC(C(F)(F)F)CC1] | | 326.2 |
| 53 | 2-(imidazo[1,2-a]pyridin-5-yl)-N-(1-methyl-3-(trifluoromethyl)-1H-pyrazol-5-yl)acetamide | 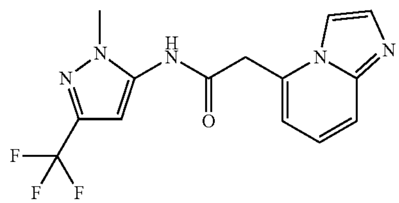 [SMILES: Cn1nc(C(F)(F)F)cc1NC(=O)Cc1cccc2nccn12] | | 324.2 |
| 54 | N-(1,5-dimethyl-1H-pyrazol-3-yl)-2-(imidazo[1,2-a]pyridin-5-yl)acetamide | 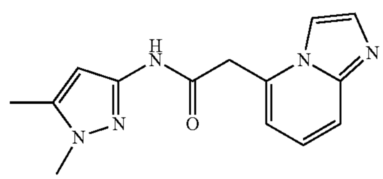 [SMILES: Cc1cc(NC(=O)Cc2cccc3nccn23)nn1C] | | 270.1 |

TABLE 1-10

| Ex. No. | IUPAC name | Structure | Salt | MS |
|---|---|---|---|---|
| 55 | N-(2-cyanoethyl)-2-(imidazo[1,2-a]pyridin-5-yl)-N-phenylacetamide | 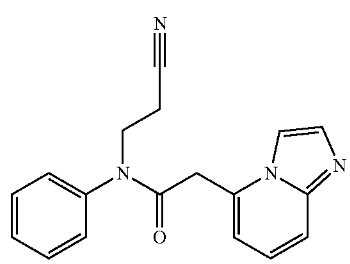 [SMILES: N#CCCN(C(=O)Cc1cccc2nccn12)c1ccccc1] | | 305.1 |
| 56 | N-(2-hydroxyethyl)-2-(imidazo[1,2-a]pyridin-5-yl)-N-phenylacetamide | 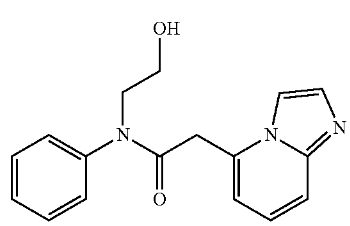 [SMILES: O=C(Cc1cccc2nccn12)N(CCO)c1ccccc1] | | 296.2 |

TABLE 1-10-continued

| Ex. No. | IUPAC name | Structure | Salt | MS |
|---|---|---|---|---|
| 57 | N-benzyl-2-(imidazo[1,2-a]pyridin-5-yl)-N-phenylacetamide | 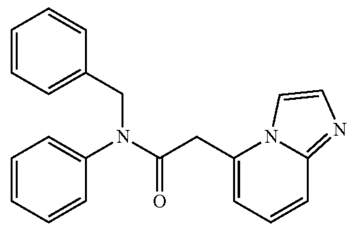 [SMILES: O=C(Cc1cccc2nccn12)N(Cc1ccccc1)c1ccccc1] | | 342.2 |
| 58 | 2-(imidazo[1,2-a]pyridin-5-yl)-N-isopropyl-N-phenylacetamide | 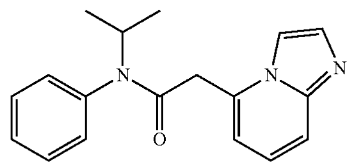 [SMILES: CC(C)N(C(=O)Cc1cccc2nccn12)c1ccccc1] | | 294.1 |
| 59 | N-ethyl-2-(imidazo[1,2-a]pyridin-5-yl)-N-(4-(trifluoromethoxy)-phenyl)acetamide | 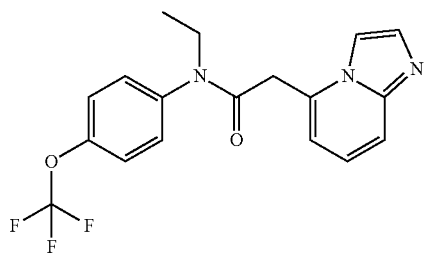 [SMILES: CCN(C(=O)Cc1cccc2nccn12)c1ccc(OC(F)(F)F)cc1] | | 364.1 |
| 60 | 2-([1,2,4]triazolo[1,5-a]pyridin-5-yl)-N-(4-(trifluoromethyl)phenyl)-acetamide | 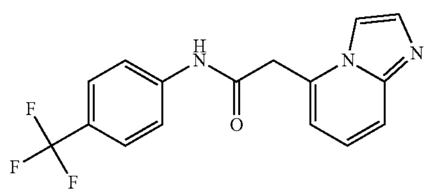 [SMILES: O=C(Cc1cccc2nccn12)Nc1ccc(C(F)(F)F)cc1] | | 321.1 |

TABLE 1-11

| Ex. No. | IUPAC name | Structure | Salt | MS |
|---|---|---|---|---|
| 61 | 2-(imidazo[1,2-a]pyrazin-5-yl)-N-(4-(trifluoromethyl)phenyl)-acetamide | 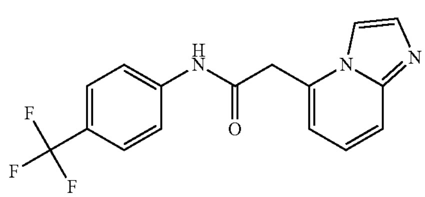 [SMILES: O=C(Cc1cccc2nccn12)Nc1ccc(C(F)(F)F)cc1] | | 319.0 |
| 62 | 2-(imidazo[1,2-a]pyridin-5-yl)-N-(4-(pentafluoro-$\lambda^6$-sulfanyl)phenyl)-acetamide | 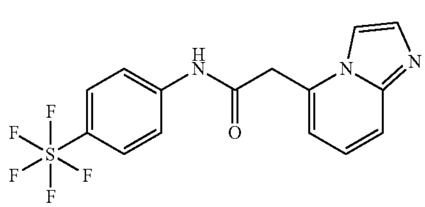 [SMILES: O=C(Cc1cccc2nccn12)Nc1ccc(S(F)(F)(F)(F)F)cc1] | | 375.9 |

TABLE 1-11-continued

| Ex. No. | IUPAC name | Structure | Salt | MS |
|---|---|---|---|---|
| 63 | 2-(imidazo[1,2-a]pyridin-5-yl)-N-(6-(trifluoromethoxy)-pyridin-3-yl)acetamide | 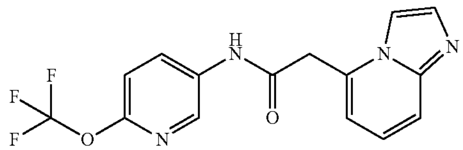 [SMILES: O=C(Cc1cccc2nccn12)Nc1ccc(OC(F)(F)F)nc1] | | 334.9 |
| 64 | N-(4-tert-butylphenyl)-2-(imidazo[1,2-a]pyridin-5-yl)acetamide | 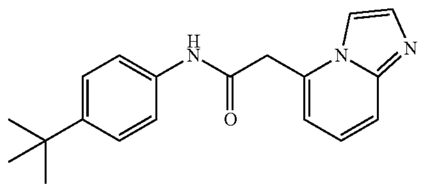 [SMILES: CC(C)(C)c1ccc(NC(=O)Cc2cccc3nccn23)cc1] | | 308.2 |
| 65 | N-(1-benzothiophen-2-yl)-2-(imidazo[1,2-a]pyridin-5-yl)acetamide | 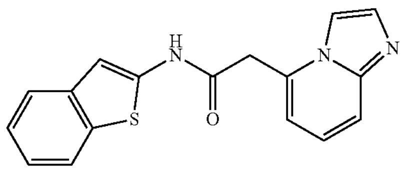 [SMILES: O=C(Cc1cccc2nccn12)Nc1cc2ccccc2s1] | | 308.1 |
| 66 | 2-(imidazo[1,2-a]pyridin-5-yl)-N-(4-isopropylphenyl)acetamide | 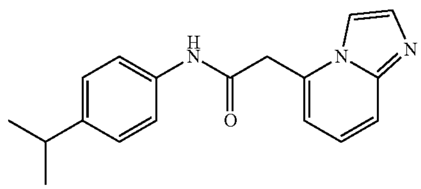 [SMILES: CC(C)c1ccc(NC(=O)Cc2cccc3nccn23)cc1] | | 294.1 |

TABLE 1-12

| Ex. No. | IUPAC name | Structure | Salt | MS |
|---|---|---|---|---|
| 67 | N-(2,3-dihydro-1-benzofuran-5-yl)-2-(imidazo[1,2-a]pyridin-5-yl)acetamide | 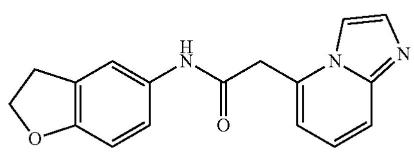 [SMILES: O=C(Cc1cccc2nccn12)Nc1ccc2c(c1)CCO2] | | 294.1 |
| 68 | 2-([1,2,4]triazolo[4,3-a]pyridin-5-yl)-N-(4-(trifluoromethyl)phenyl)-acetamide | 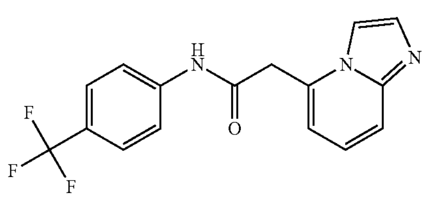 [SMILES: O=C(Cc1cccc2nccn12)Nc1ccc(C(F)(F)F)cc1] | | 318.9 |
| 69 | N-(4-(difluoromethyl)phenyl)-2-(imidazo[1,2-a]pyridin-5-yl)acetamide | 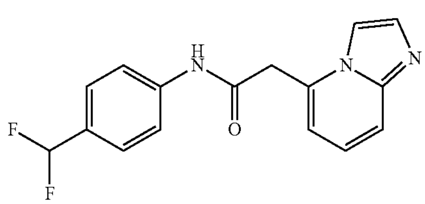 [SMILES: O=C(Cc1cccc2nccn12)Nc1ccc(C(F)F)cc1] | | 302.1 |

TABLE 1-12-continued

| Ex. No. | IUPAC name | Structure | Salt | MS |
|---|---|---|---|---|
| 70 | N-(2,3-dihydro-1-benzofuran-6-yl)-2-(imidazo[1,2-a]pyridin-5-yl)acetamide | 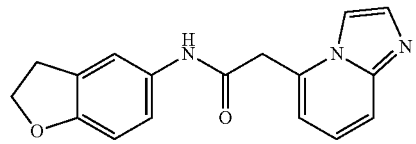 [SMILES: O=C(Cc1cccc2nccn12)Nc1ccc2c(c1)CCO2] | | 294.1 |
| 71 | 2-(7-methylimidazo(1,2-a]pyridin-5-yl)-N-(4-(trifluoromethyl)phenyl)-acetamide | 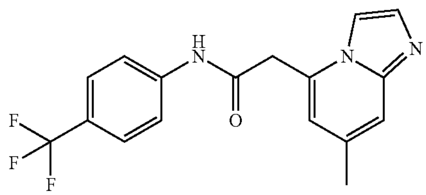 [SMILES: Cc1cc(CC(=O)Nc2ccc(C(F)(F)F)cc2)n2ccnc2c1] | | 332.0 |
| 72 | N-(4-(3-fluoroazetidin-1-yl)phenyl)-2-(imidazo[1,2-a]pyridin-5-yl)acetamide | 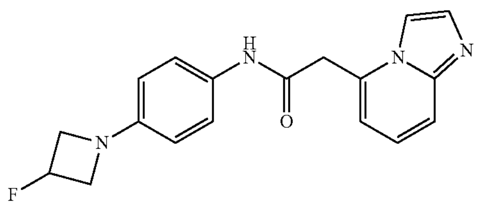 [SMILES: O=C(Cc1cccc2nccn12)Nc1ccc(N2CC(F)C2)cc1] | | 325.2 |

TABLE 1-13

| Ex. No. | IUPAC name | Structure | Salt | MS |
|---|---|---|---|---|
| 73 | 2-(6-fluoroimidazo[1,2-a]pyridin-5-yl)-N-(4-(trifluoromethyl)phenyl)-acetamide | 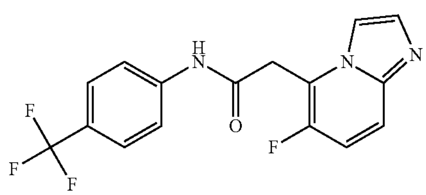 [SMILES: O=C(Cc1c(F)ccc2nccn12)Nc1ccc(C(F)(F)F)cc1] | | 335.9 |
| 74 | N-(3-fluoro-4-(oxetan-3-yloxy)phenyl)-2-(imidazo[1,2-a]pyridin-5-yl)acetamide | 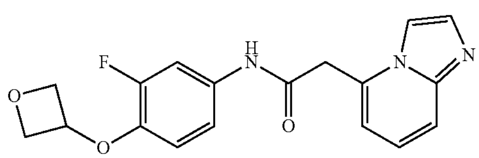 [SMILES: O=C(Cc1cccc2nccn12)Nc1ccc(OC2COC2)c(F)c1] | | 342.1 |
| 75 | N-(4-(cyclobutyloxy)phenyl)-2-(imidazo[1,2-a]pyridin-5-yl)acetamide | 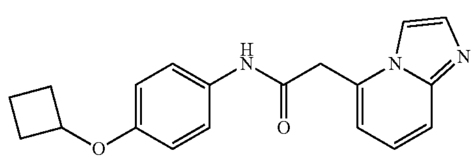 [SMILES: O=C(Cc1cccc2nccn12)Nc1ccc(OC2CCC2)cc1] | | 322.2 |
| 76 | N-(1,2-benzoxazol-3-yl)-2-(imidazo[1,2-a]pyridin-5-yl)acetamide | 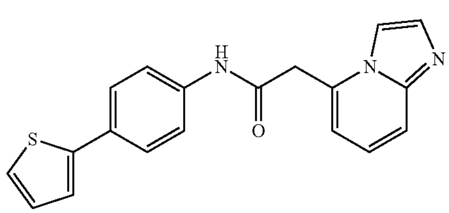 [SMILES: O=C(Cc1cccc2nccn12)Nc1ccc(-c2cccs2)cc1] | | 293.1 |

| Ex. No. | IUPAC name | Structure | Salt | MS |
|---|---|---|---|---|
| 77 | 2-(imidazo[1,2-a]pyridin-5-yl)-N-(4-(2-thienyl)phenyl)acetamide | 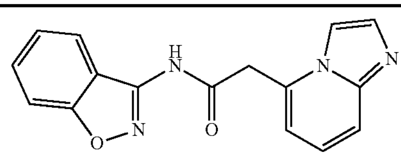 | | 334.1 |

Example 78

2-(6-ethylimidazo[1,2-a]pyridin-5-yl)-N-(4-(trifluoromethoxy)phenyl)acetamide (A) 5-iodo-6-methylpyridin-2-amine To a solution of 6-methylpyridin-2-amine (10 g, 0.092 mol) in DMF (50 mL) was added N-iodosuccinimide (15 g, 0.13 mol), and the mixture was stirred at room temperature overnight. The reaction mixture was diluted with water (200 mL), and the precipitated solid was collected by filtration and washed with ethyl acetate to give the title compound (7.5 g).

MS: [M+H]$^+$ 235.0

(B) 6-iodo-5-methylimidazo[1,2-a]pyridine

To a solution of 5-iodo-6-methylpyridin-2-amine (7.5 g, 32 mmol) in ethanol (400 mL) was added 2-chloroacetaldehyde aqueous solution (18 mL, 40%), and the mixture was stirred at 80° C. for 16 hr. After cooling, the reaction mixture was concentrated under reduced pressure, and the residue was diluted with water, neutralized with 30% aqueous sodium hydroxide solution, and extracted with dichloromethane (150 mL×3). The obtained organic layer was dried over anhydrous sodium sulfate, and the solvent was evaporated under reduced pressure. The obtained solid was washed with ethyl acetate to give the title compound (6.0 g).

MS: [M+H]$^+$ 259.1

(C) 5-methyl-6-vinylimidazo[1,2-a]pyridine

A mixture of 6-iodo-5-methylimidazo[1,2-a]pyridine (6.0 g, 23 mmol), potassium vinyltrifluoroborate (4.7 g, 35 mmol), potassium carbonate (6.4 g, 47 mmol), 1,1'-bis(diphenylphosphino)ferrocene-palladium(II) dichloride (500 mg), dioxane (200 mL) and water (1.5 mL) was stirred under a nitrogen atmosphere at 80° C. for 16 hr. The reaction mixture was concentrated under reduced pressure, and the residue was purified by silica gel column chromatography (dichloromethane/methanol) to give the title compound (2.8 g).

MS: [M+H]$^+$ 159.3

(D) 6-ethyl-5-methylimidazo[1,2-a]pyridine

To a solution of 5-methyl-6-vinylimidazo[1,2-a]pyridine (2.8 g, 18 mmol) in methanol (200 mL) was added Pd/C (400 mg), and the mixture was stirred under a hydrogen gas atmosphere at room temperature for 16 hr. The reaction mixture was filtered, and the solvent was evaporated under reduced pressure to give the title compound (2.5 g).

MS: [M+H]$^+$ 161.3

(E) (6-ethylimidazo[1,2-a]pyridin-5-yl)acetic acid

Under a nitrogen gas atmosphere, to a solution of 6-ethyl-5-methylimidazo[1,2-a]pyridine (2.5 g, 16 mmol) in THF (200 mL) was added dropwise lithium diisopropylamide (1 M, 16 mL, 16 mmol) at −78° C. The reaction mixture was stirred at −78° C. for 1 hr and dry ice (5.0 g) was added. The reaction mixture was heated to room temperature, stirred for 16 hr and neutralized with 2M hydrochloric acid. The mixture was purified by HPLC (L-column 2 ODS, acetonitrile/water, containing ammonium acetate) and the obtained fraction was concentrated under reduced pressure. To the residue was added saturated aqueous sodium hydrogen carbonate solution, and the mixture was extracted with ethyl acetate. The extract was dried over anhydrous sodium sulfate, and the solvent was evaporated under reduced pressure to give the title compound (1.8 g).

$^1$H NMR (400 MHz, DMSO-d$_6$): δ 1.13 (3H, t, J=7.6 Hz), 2.63 (2H, q, J=7.6 Hz), 3.95 (2H, s), 7.14 (1H, d, J=9.2 Hz), 7.43 (1H, d, J=9.2 Hz), 7.52 (1H, d, J=0.8 Hz), 7.76 (1H, s).

(F) 2-(6-ethylimidazo[1,2-a]pyridin-5-yl)-N-(4-(trifluoromethoxy)phenyl)acetamide To a solution of (6-ethylimidazo[1,2-a]pyridin-5-yl)acetic acid (100 mg, 0.49 mmol), 4-(trifluoromethoxy)aniline (130 mg, 0.74 mmol) in pyridine (10 mL) was added HATU (370 mg, 0.98 mmol) and the mixture was stirred at room temperature for 16 hr. The reaction mixture was concentrated under reduced pressure, and the residue was purified by silica gel column chromatography (dichloromethane/methanol) to give the title compound (105 mg).

$^1$H NMR (400 MHz, DMSO-d$_6$): δ 1.16 (3H, t, J=7.6 Hz), 2.68 (2H, q, J=7.2 Hz), 4.23 (2H, s), 7.18 (1H, d, J=9.2 Hz), 7.32 (2H, d, J=8.4 Hz), 7.49 (1H, d, J=9.2 Hz), 7.54 (1H, s), 7.68 (2H, d, J=9.2 Hz), 7.85 (1H, s), 10.67 (1H, s).

Example 79

2-(6-methylimidazo[1,2-a]pyridin-5-yl)-N-(4-(trifluoromethoxy)phenyl)acetamide (A) 5,6-dimethylimidazo[1,2-a]pyridine A mixture of 5,6-dimethylpyridin-2-amine (2.0 g, 16 mmol), 40% chloroacetaldehyde aqueous solution (3.2 mL, 20 mmol) and ethanol (40 mL) was heated under reflux overnight. The solvent was evaporated under reduced pressure, and the reaction mixture was neutralized with saturated aqueous sodium hydrogen carbonate solution, and extracted with ethyl acetate. The organic layer was dried over anhydrous magnesium sulfate, and the residue was purified by NH silica gel column chromatography (hexane/ethyl acetate) to give the title compound (2.5 g).

$^1$H NMR (300 MHz, CDCl$_3$) δ2.35 (3H, s), 2.53 (3H, s), 7.05 (1H, d, J=9.4 Hz), 7.46 (2H, t, J=4.5 Hz), 7.65 (1H, d, J=1.1 Hz).

(B) methyl (6-methylimidazo[1,2-a]pyridin-5-yl)acetate

To a solution of diisopropylamine (4.3 mL, 31 mmol) in THF (30 mL) was added n-butyllithium (1.6 M hexane solution, 17 mL, 27 mmol) at −78° C., and the mixture was stirred at the same temperature for 30 min. A solution of 5,6-dimethylimidazo[1,2-a]pyridine (3.0 g, 21 mmol) in THF (30 mL) was added dropwise to the reaction mixture. The reaction mixture was stirred at −78° C. for 1 hr and at −40° C. for 1 hr, cooled to −78° C. and dry ice was added. The reaction mixture was heated to room temperature, and the solvent was evaporated under reduced pressure. The residue was diluted with 2 M aqueous sodium hydroxide solution. The aqueous layer was washed 3 times with ethyl acetate, acidified with 2 M hydrochloric acid, and concentrated under reduced pressure. The obtained residue was treated with methanol and ethyl acetate, and the insoluble material was filtered off. The filtrate was concentrated under reduced pressure to give crude (6-methylimidazo[1,2-a]pyridin-5-yl)acetic acid hydrochloride.

A mixture of the obtained crude (6-methylimidazo[1,2-a]pyridin-5-yl)acetic acid hydrochloride, sulfuric acid (2 mL, 38 mmol) and methanol (100 mL) was heated under reflux for 3 hr. The solvent was evaporated under reduced pressure, and the residue was neutralized with saturated aqueous sodium hydrogen carbonate solution, and extracted with ethyl acetate. The organic layer was washed with water, and concentrated under reduced pressure. The residue was purified by NH silica gel column chromatography (hexane/ethyl acetate) to give the title compound (2.7 g).

$^1$H NMR (300 MHz, DMSO-d$_6$) δ2.29 (3H, s), 3.64 (3H, s), 4.22 (2H, s), 7.15 (1H, d, J=9.0 Hz), 7.47 (1H, d, J=9.0 Hz), 7.56 (1H, d, J=0.8 Hz), 7.82 (1H, s).

(C) (6-methylimidazo[1,2-a]pyridin-5-yl)acetic acid hydrochloride

A solution of methyl (6-methylimidazo[1,2-a]pyridin-5-yl)acetate (2.4 g, 12 mmol) in 6 M hydrochloric acid (50 mL, 300 mmol) was heated under reflux overnight. The reaction mixture was concentrated under reduced pressure to give the title compound (2.7 g).

$^1$H NMR (300 MHz, DMSO-d$_6$) δ2.42 (3H, s), 4.36 (2H, s), 7.88 (2H, s), 8.25 (1H, d, J=2.2 Hz), 8.45 (1H, d, J=2.2 Hz), 13.17 (1H, brs), 14.03-15.27 (1H, m).

(D) 2-(6-methylimidazo[1,2-a]pyridin-5-yl)-N-(4-(trifluoromethoxy)phenyl)acetamide A mixture of (6-methylimidazo[1,2-a]pyridin-5-yl)acetic acid hydrochloride (200 mg, 0.88 mmol), 4-(trifluoromethoxy)aniline (0.12 mL, 0.88 mmol), 1-ethyl-3-(3-dimethylaminopropyl)carbodiimide hydrochloride (250 mg, 1.3 mmol), HOBt monohydrate (140 mg, 0.88 mmol), triethylamine (0.37 mL, 2.7 mmol) and DMF (1 mL) was stirred at room temperature overnight. The residue was purified by NH silica gel column chromatography (ethyl acetate/methanol) to give the title compound (250 mg).

$^1$H NMR (300 MHz, DMSO-d$_6$) δ2.34 (3H, s), 4.22 (2H, s), 7.16 (1H, d, J=9.2 Hz), 7.33 (2H, d, J=8.3 Hz), 7.46 (1H, d, J=9.2 Hz), 7.55 (1H, d, J=1.2 Hz), 7.65-7.76 (2H, m), 7.88 (1H, s), 10.64 (1H, s).

Example 80

2-(6-methoxyimidazo[1,2-a]pyridin-5-yl)-N-(4-(trifluoromethoxy)phenyl)acetamide (A) 6-methoxy-5-methylimidazo[1,2-a]pyridine A mixture of 5-methoxy-6-methylpyridin-2-amine (5.0 g, 36 mmol), 40% chloroacetaldehyde aqueous solution (7.1 mL, 43 mmol) and ethanol (100 mL) was heated under reflux overnight. The solvent was evaporated under reduced pressure, and the reaction mixture was neutralized with saturated aqueous sodium hydrogen carbonate solution, and extracted with ethyl acetate. The solvent was evaporated under reduced pressure and the residue was purified by NH silica gel column chromatography (hexane/ethyl acetate) to give the title compound (5.8 g).

$^1$H NMR (300 MHz, CDCl$_3$) δ2.52 (3H, s), 3.87 (3H, s), 7.16 (1H, d, J=9.7 Hz), 7.45 (1H, d, J=0.9 Hz), 7.52 (1H, d, J=9.7 Hz), 7.69 (1H, d, J=1.1 Hz).

(B) methyl 2-(6-methoxyimidazo[1,2-a]pyridin-5-yl)acetate

To a solution of diisopropylamine (2.6 mL, 19 mmol) in THF (20 mL) was added n-butyllithium (1.6 M hexane solution, 10 mL, 16 mmol) at −78° C., and the mixture was stirred at the same temperature for 30 min. A solution of 6-methoxy-5-methylimidazo[1,2-a]pyridine (2.0 g, 12 mmol) in THF (30 mL) was added dropwise to the reaction mixture. The reaction mixture was stirred at −78° C. for 1 hr and at −40° C. for 1 hr, cooled to −78° C. and dry ice was added. The reaction mixture was heated to room temperature, and the solvent was evaporated under reduced pressure. The residue was diluted with water and ethyl acetate. The aqueous layer was washed with ethyl acetate, acidified with 2 M hydrochloric acid, and concentrated under reduced pressure to give crude (6-methylimidazo[1,2-a]pyridin-5-yl)acetic acid hydrochloride.

A mixture of the obtained crude (6-methylimidazo[1,2-a]pyridin-5-yl)acetic acid hydrochloride, p-toluenesulfonic acid monohydrate (0.10 g, 0.53 mmol) and methanol (100 mL) was heated under reflux overnight. The solvent was evaporated under reduced pressure, and the residue was purified by NH silica gel column chromatography (hexane/ethyl acetate) to give the title compound (0.55 g).

$^1$H NMR (300 MHz, CDCl$_3$) δ3.67-3.74 (3H, m), 3.91 (3H, s), 4.06 (2H, s), 7.19 (1H, d, J=9.8 Hz), 7.48 (1H, d, J=0.8 Hz), 7.57-7.65 (1H, m), 7.68 (1H, d, J=1.2 Hz).

(C) 2-(6-methoxyimidazo[1,2-a]pyridin-5-yl)acetic acid hydrochloride

A solution of methyl 2-(6-methoxyimidazo[1,2-a]pyridin-5-yl)acetate (0.55 g, 2.5 mmol) in 6 M hydrochloric acid (30 mL, 180 mmol) was heated under reflux overnight. The reaction mixture was concentrated under reduced pressure to give the title compound (0.60 g).

$^1$H NMR (300 MHz, DMSO-d$_6$) δ3.95-3.98 (3H, m), 4.24-4.28 (2H, m), 7.94-8.02 (1H, m), 8.04-8.13 (1H, m), 8.29 (1H, d, J=2.2 Hz), 8.47 (1H, d, J=1.9 Hz), 13.83-15.19 (1H, m).

(D) 2-(6-methoxyimidazo[1,2-a]pyridin-5-yl)-N-(4-(trifluoromethoxy)phenyl)acetamide A mixture of 2-(6-methoxyimidazo[1,2-a]pyridin-5-yl) acetic acid hydrochloride (300 mg, 1.2 mmol), 4-(trifluoromethoxy)aniline (0.17 mL, 1.2 mmol), 1-ethyl-3-(3-dimethylaminopropyl)carbodiimide hydrochloride (360 mg, 1.9 mmol), HOBt monohydrate (190 mg, 1.2 mmol), triethylamine (0.52 mL, 3.7 mmol) and DMF (1 mL) was stirred at room temperature overnight. To the reaction mixture was added water, and the mixture was extracted with ethyl acetate. The organic layer was washed with water and dried over anhydrous magnesium sulfate. The solvent was evaporated under reduced pressure. The residue was recrystallized from ethyl acetate to give the title compound (100 mg).

$^1$H NMR (300 MHz, DMSO-$d_6$) δ3.84 (3H, s), 4.19 (2H, s), 7.32 (2H, d, J=8.3 Hz), 7.38 (1H, d, J=9.8 Hz), 7.53-7.61 (2H, m), 7.64-7.76 (2H, m), 7.85 (1H, s), 10.59 (1H, s).

The compounds of Examples 81-99 in the following Tables were produced according to the methods shown in the above-mentioned Examples, or a method analogous thereto. The Example compounds are shown in the following Tables. In the Tables, MS shows measured values.

TABLE 2-1

| Ex. No. | IUPAC name | Structure | Salt | MS |
|---|---|---|---|---|
| 78 | 2-(6-ethylimidazo[1,2-a]pyridin-5-yl)-N-(4-(trifluoromethoxy)phenyl)acetamide | 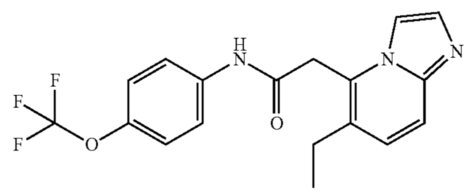 [SMILES: CCc1ccc2nccn2c1CC(=O)Nc1ccc(OC(F)(F)F)cc1] | | 364.1 |
| 79 | 2-(6-methylimidazo[1,2-a]pyridin-5-yl)-N-(4-(trifluoromethoxy)phenyl)acetamide | 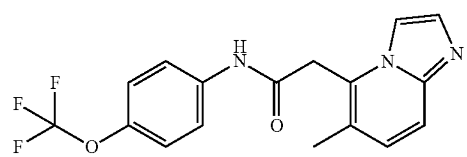 [SMILES: Cc1ccc2nccn2c1CC(=O)Nc1ccc(OC(F)(F)F)cc1] | | 350.0 |
| 80 | 2-(6-methoxyimidazo[1,2-a]pyridin-5-yl)-N-(4-(trifluoromethoxy)phenyl)acetamide | 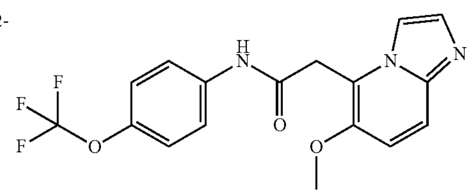 | | 366.1 |
| 81 | 2-(6-ethylimidazo[1,2-a]pyridin-5-yl)-N-(4-(trifluoromethyl)phenyl)acetamide | 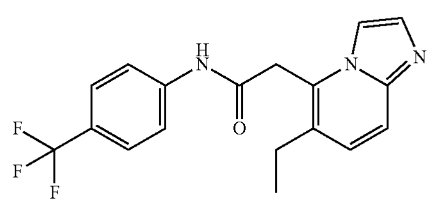 [SMILES: CCc1ccc2nccn2c1CC(=O)Nc1ccc(C(F)(F)F)cc1] | | 348.2 |
| 82 | N-(3-fluoro-4-iodophenyl)-2-(imidazo[1,2-a]pyridin-5-yl)acetamide | 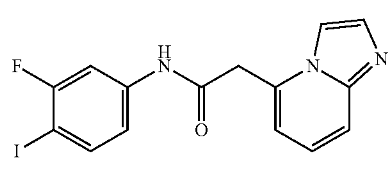 [SMILES: O=C(Cc1cccc2nccn12)Nc1ccc(I)c(F)c1] | | 396.0 |
| 83 | N-(4-bromo-3-fluorophenyl)-2-(imidazo[1,2-a]pyridin-5-yl)acetamide | 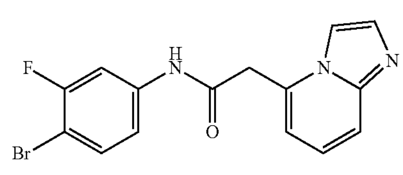 [SMILES: O=C(Cc1cccc2nccn12)Nc1ccc(Br)c(F)c1] | | 348.1 |

TABLE 2-2

| Ex. No. | IUPAC name | Structure | Salt | MS |
|---|---|---|---|---|
| 84 | 2-(imidazo[1,2-a]pyridin-5-yl)-N-(4-(trifluoromethoxy)phenyl)propanamide | 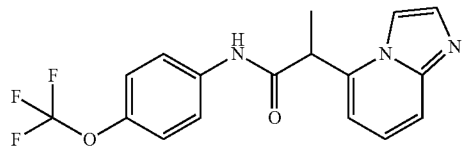 [SMILES: CC(C(=O)Nc1ccc(OC(F)(F)F)cc1)c1cccc2nccn12] | | 350.0 |
| 85 | 2-(2-methylimidazo[1,2-a]pyridin-5-yl)-N-(4-(trifluoromethoxy)phenyl)acetamide | 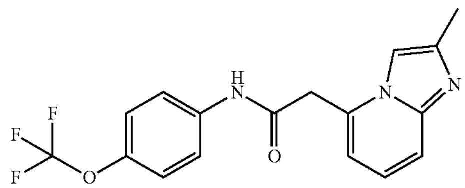 [SMILES: Cc1cn2c(CC(=O)Nc3ccc(OC(F)(F)F)cc3)cccc2n1] | | 350.0 |
| 86 | 2-(7-fluoroimidazo[1,2-a]pyridin-5-yl)-N-(4-(trifluoromethoxy)phenyl)acetamide | 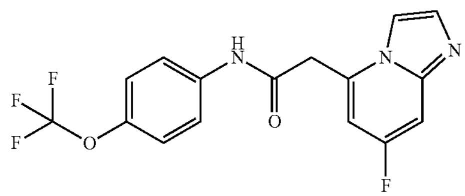 [SMILES: O=C(Cc1cc(F)cc2nccn12)Nc1ccc(OC(F)(F)F)cc1] | | 354.1 |
| 87 | 2-(6-methylimidazo[1,2-a]pyridin-5-yl)-N-(4-(trifluoromethyl)phenyl)acetamide | 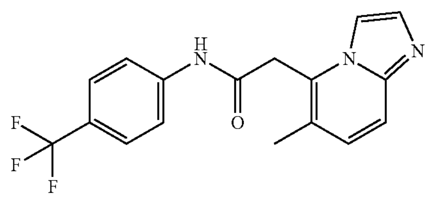 [SMILES: Cc1ccc2nccn2c1CC(=O)Nc1ccc(C(F)(F)F)cc1] | | 332.0 |
| 88 | N-(4-bromophenyl)-2-(imidazo[1,2-a]pyridin-5-yl)acetamide | 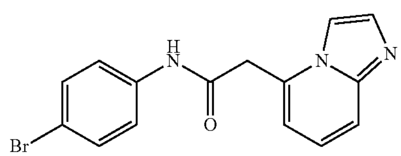 [SMILES: O=C(Cc1cccc2nccn12)Nc1ccc(Br)cc1] | | 330.0 |
| 89 | 2-(6-methoxyimidazo[1,2-a]pyridin-5-yl)-N-(4-(trifluoromethyl)phenyl)acetamide | 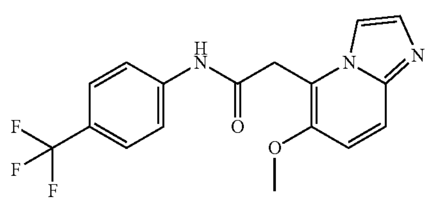 [SMILES: COc1ccc2nccn2c1CC(=O)Nc1ccc(C(F)(F)F)cc1] | | 350.2 |

TABLE 2-3

| Ex. No. | IUPAC name | Structure | Salt | MS |
|---|---|---|---|---|
| 90 | 2-(7-fluoroimidazo[1,2-a]pyridin-5-yl)-N-(4-(trifluoromethyl)phenyl)acetamide | 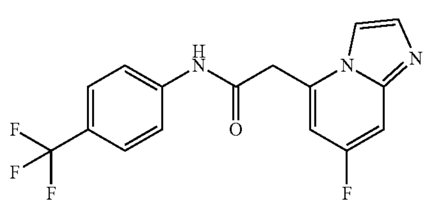 | | 336.0 |

TABLE 2-3-continued

| Ex. No. | IUPAC name | Structure | Salt | MS |
|---|---|---|---|---|
| 91 | 2-(6-chloroimidazo[1,2-a]pyridin-5-yl)-N-(4-(trifluoromethoxy)phenyl)acetamide | 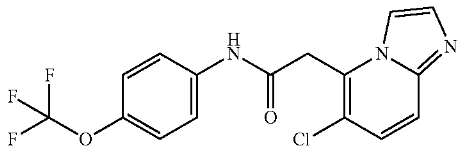 [SMILES: O=C(Cc1c(Cl)ccc2nccn12)Nc1ccc(OC(F)(F)F)cc1] | | 370.0 |
| 92 | 2-(imidazo[1,2-a]pyridin-5-yl)-N-(5-(trifluoromethoxy)pyridin-2-yl)acetamide | 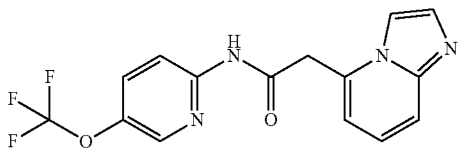 [SMILES: O=C(Cc1cccc2nccn12)Nc1ccc(OC(F)(F)F)cn1] | | 337.1 |
| 93 | 2-(imidazo[1,2-a]pyridin-5-yl)-N-(4-(trifluoromethyl)phenyl)propanamide | 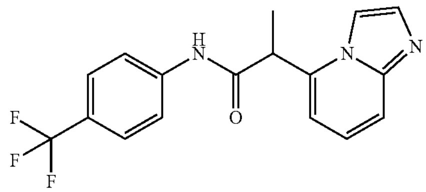 [SMILES: CC(C(=O)Nc1ccc(C(F)(F)F)cc1)c1cccc2nccn12] | | 334.1 |
| 94 | 2-(8-fluoroimidazo[1,2-a]pyridin-5-yl)-N-(4-(trifluoromethoxy)phenyl)acetamide | 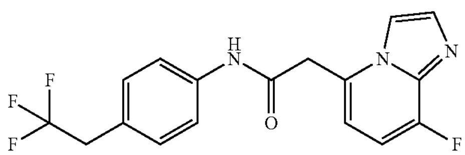 [SMILES: O=C(Cc1ccc(F)c2nccn12)Nc1ccc(CC(F)(F)F)cc1] | | 354.1 |
| 95 | N-(5-ethylpyridin-2-yl)-2-(imidazo[1,2-a]pyridin-5-yl)acetamide | 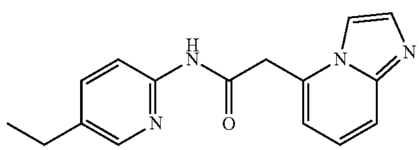 [SMILES: CCc1ccc(NC(=O)Cc2cccc3nccn23)nc1] | | 281.1 |

TABLE 2-4

| Ex. No. | IUPAC name | Structure | Salt | MS |
|---|---|---|---|---|
| 96 | N-(2,5-difluoro-4-methoxyphenyl)-2-(imidazo[1,2-a]pyridin-5-yl)acetamide | 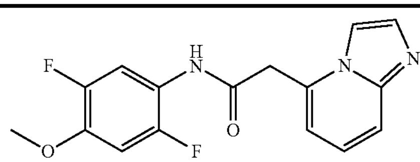 | | 318.1 |
| 97 | 2-(8-fluoroimidazo[1,2-a]pyridin-5-yl)-N-{4-(trifluoromethyl)phenyl}acetamide | 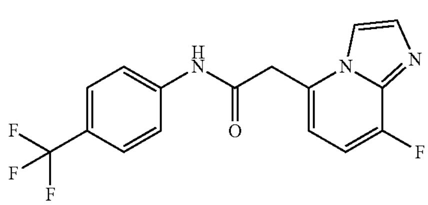 [SMILES: O=C(Cc1ccc(F)c2nccn12)Nc1ccc(C(F)(F)F)cc1] | | 335.9 |
| 98 | 2-(6-chloroimidazo[1,2-a]pyridin-5-yl)-N-(4-(trifluoromethyl)phenyl)acetamide | 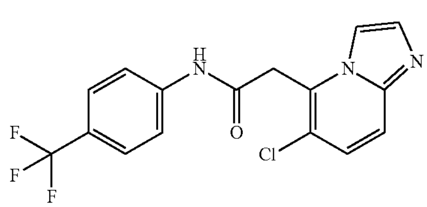 [SMILES: O=C(Cc1c(Cl)ccc2nccn12)Nc1ccc(C(F)(F)F)cc1] | | 354.0 |

TABLE 2-4-continued

| Ex. No. | IUPAC name | Structure | Salt | MS |
|---|---|---|---|---|
| 99 | N-(6-ethylpyridin-3-yl)-2-(imidazo[1,2-a]pyridin-5-yl)acetamide | 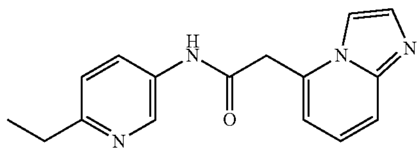 [SMILES: CCc1ccc(NC(=O)Cc2cccc3nccn23)cn1] | | 281.1 |

Experimental Example 1 NR2B $Ca^{2+}$ Flux Assay

Human GRIN1 and human GRIN2B expressing HEK293 cells were purchased from ChanTest. The cells were cultured in a DMEM/F-12 (COSMO BIO, 10-092-CM) medium added with 10% FBS (fetal bovine serum, AusGene), 100 units/mL penicillin, 100 μg/mL streptomycin, 500 μg/mL neomycin, 100 μg/mL Zeocin, 5 μg/mL Blasticidin at 37° C., 5% $CO_2$. The cells were detached from flask with trypsin the day before the assay, suspended in a seeding medium (DMEM (Invitrogen, 31053) added with 10% FBS, 100 units/mL penicillin, 100 μg/mL streptomycin) at $8 \times 10^5$ cells/mL, seeded by 25 μL per well in a 384-well plate (Falcon, 356663) at 20000 cells/well, and cultured overnight in an incubator. On the day of the assay, tetracycline (Wako Pure Chemical Industries, Ltd., 209-16561) was diluted with the seeding medium at 2 μg/mL, added at 25 μg/mL to the plate seeded with the cells, and cultured for 2 hr in an incubator. Thereafter, the medium was removed, and the cells were washed with 50 μL/well assay buffer (137 mM NaCl, 4 mM KCl, 1.8 mM $CaCl_2$, 10 mM HEPES (pH 7.2), 10 mM Glucose, 0.1% BSA). Then, a loading buffer (assay buffer added with 2.5 uM Fluo-4AM, 2 mM Amaranth, 1 mM Tartrazine) was added at 25 μL/well, and loading was performed in the incubator for 30 min, and at room temperature for 15 min. A test compound (25 μL) was added, and the cells were stood for 15 min at room temperature. Using FLIPR (Molecular Devices), 25 μL of an assay buffer containing μM glutamic acid, 30 μM glycine was added, and the fluorescence signal was measured every 3 seconds for 5 min. The inhibitory activity was calculated as a relative activity value that inhibits 100% of the cumulative value of the fluorescence value of a well added with a buffer free of glutamic acid, glycine, relative to the cumulative value of the fluorescence value of each well. The results are shown in the following Table 3.

TABLE 3

| Example No. | inhibitory rate (@10 μM) |
|---|---|
| 1 | 91% |
| 2 | 91% |
| 3 | 94% |
| 4 | 94% |
| 5 | 93% |
| 6 | 93% |
| 7 | 90% |
| 8 | 92% |
| 9 | 87% |
| 10 | 91% |
| 11 | 94% |
| 12 | 93% |
| 13 | 88% |
| 14 | 92% |
| 15 | 91% |
| 16 | 91% |
| 17 | 93% |
| 18 | 91% |
| 19 | 91% |
| 20 | 74% |
| 21 | 56% |
| 23 | 81% |
| 24 | 62% |
| 26 | 53% |
| 27 | 66% |
| 29 | 88% |
| 30 | 50% |
| 31 | 78% |
| 32 | 83% |
| 33 | 92% |
| 34 | 71% |
| 35 | 90% |
| 36 | 80% |
| 37 | 81% |
| 38 | 82% |
| 39 | 90% |
| 43 | 90% |
| 44 | 71% |
| 47 | 52% |
| 51 | 56% |
| 59 | 57% |
| 62 | 82% |
| 63 | 85% |
| 64 | 84% |
| 65 | 83% |
| 66 | 92% |
| 67 | 78% |
| 69 | 87% |
| 70 | 60% |
| 71 | 51% |
| 73 | 73% |
| 75 | 68% |
| 78 | 97% |
| 79 | 95% |
| 80 | 94% |
| 81 | 95% |
| 82 | 94% |
| 83 | 93% |
| 84 | 94% |
| 85 | 91% |
| 86 | 93% |
| 87 | 93% |
| 88 | 91% |
| 89 | 92% |
| 90 | 88% |
| 91 | 91% |
| 92 | 87% |
| 93 | 89% |
| 94 | 85% |
| 95 | 76% |

| | | |
|---|---|---|
| 1) compound of Example 1 | 30 mg | |
| 2) finely-powdered cellulose | 10 mg | |
| 3) lactose | 19 mg | |
| 4) magnesium stearate | 1 mg | |
| total | 60 mg | |

Formulation Example 1 (Production of Capsule)

1), 2), 3) and 4) are mixed and filled in a gelatin capsule.

Formulation Example 2 (Production of Tablets)

| | | |
|---|---|---|
| 1) compound of Example 1 | 30 g | |
| 2) lactose | 50 g | |
| 3) cornstarch | 15 g | |
| 4) calcium carboxymethylcellulose | 44 g | |
| 5) magnesium stearate | 1 g | |
| 1000 tablets total | 140 g | |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention has an antagonistic action on an NMDA receptor containing the NR2B subunit, and is useful as a prophylactic or therapeutic agent for major depression, bipolar disorder, migraine, pain, peripheral symptoms of dementia and the like.

This application is based on patent application No. 2014-259662 filed in Japan, the contents of which are encompassed in full herein.

The invention claimed is:

1. A compound represented by the formula (I):

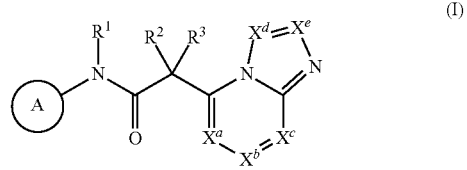

wherein
ring A is a benzene ring optionally further substituted by 1 to 3 substituents selected from
  (1) a C1-6 alkoxy group optionally substituted by 1 to 3 halogen atoms,
  (2) a C1-6 alkyl group optionally substituted by 1 to 3 halogen atoms,
  (3) a halogen atom, and
  (4) a C3-10 cycloalkyl group;
$R^1$, $R^2$ and $R^3$ are each a hydrogen atom;
$X^a$ is $CR^a$;
$X^b$ is $CR^b$;
$X^c$ is $CR^c$;
$X^d$ is $CR^d$;
$X^e$ is $CR^e$; and
$R^a$ is a hydrogen atom, a $C_{1-6}$ alkyl group or a $C_{1-6}$ alkoxy group; and
$R^b$, $R^c$, $R^d$ and $R^e$ are each a hydrogen atom,
or a salt thereof.

2. 2-(Imidazo[1,2-a]pyridin-5-yl)-N-(4-(trifluoromethyl)phenyl)acetamide or a salt thereof.

3. 2-(Imidazo[1,2-a]pyridin-5-yl)-N-(4-methoxyphenyl)acetamide or a salt thereof.

4. N-(3-fluoro-4-methoxyphenyl)-2-(imidazo[1,2-a]pyridin-5-yl)acetamide or a salt thereof.

5. A medicament comprising the compound according to claim 1, or a salt thereof.

6. A method for the treatment of major depression, bipolar disorder, migraine, pain, or peripheral symptoms of dementia in a mammal, comprising administering an effective amount of the compound according to claim 1 or a salt thereof to the mammal.

* * * * *